United States Patent
Gagnon et al.

(10) Patent No.: US 11,224,396 B2
(45) Date of Patent: Jan. 18, 2022

(54) METHOD AND APPARATUS FOR IMPROVING SCATTER ESTIMATION AND CORRECTION IN IMAGING

(71) Applicant: Accuray, Inc., Sunnyvale, CA (US)

(72) Inventors: Daniel Gagnon, Twinsburg, OH (US); Chuanyong Bai, Solon, OH (US); Zhicong Yu, Highland Hts., OH (US); Amit Jain, Solon, OH (US); Calvin R. Maurer, Jr., San Jose, CA (US)

(73) Assignee: Accuray, Inc., Sunnyvale, CA (US)

( * ) Notice: Subject to any disclaimer, the term of this patent is extended or adjusted under 35 U.S.C. 154(b) by 43 days.

(21) Appl. No.: 16/694,218

(22) Filed: Nov. 25, 2019

(65) Prior Publication Data

US 2020/0170601 A1 Jun. 4, 2020

Related U.S. Application Data

(60) Provisional application No. 62/773,712, filed on Nov. 30, 2018, provisional application No. 62/773,700, (Continued)

(51) Int. Cl.
*A61B 6/00* (2006.01)
*G06T 11/00* (2006.01)
(Continued)

(52) U.S. Cl.
CPC ............ *A61B 6/5282* (2013.01); *A61B 6/027* (2013.01); *A61B 6/032* (2013.01); *A61B 6/06* (2013.01);
(Continued)

(58) Field of Classification Search
CPC ..... A61B 6/5282; A61B 6/405; A61B 6/5205; A61B 6/027; A61B 6/469; A61B 6/032;
(Continued)

(56) References Cited

U.S. PATENT DOCUMENTS 4,190,773 A 2/1980 Braden et al.
5,615,279 A 3/1997 Yoshioka et al.
(Continued)

FOREIGN PATENT DOCUMENTS

DE 10 2006 007058 A1 7/2007
EP 1062914 A1 12/2000
(Continued)

OTHER PUBLICATIONS

International Search Report and Written Opinion from PCT/US2019/063080 dated Mar. 16, 2020.
(Continued)

*Primary Examiner* — Chih-Cheng Kao
(74) *Attorney, Agent, or Firm* — Calfee, Halter & Griswold LLP

(57) ABSTRACT

An x-ray imaging apparatus and associated methods are provided to receive measured projection data from a wide aperture scan of a wide axial region and a narrow aperture scan of a narrow axial region within the wide axial region and determine an estimated scatter in the wide axial region using an optimized scatter estimation technique. The optimized scatter estimation technique is based on the difference between the measured scatter in the narrow axial region and the estimated scatter in the narrow axial region. Kernel-based scatter estimation/correction techniques can be fitted to minimize the scatter difference in the narrow axial region and thereafter applying the fitted (optimized) kernel-based scatter estimation/correction to the wide axial region. Optimizations can occur in the projection data domain or the reconstruction domain. Iterative processes are also utilized.

20 Claims, 11 Drawing Sheets

Related U.S. Application Data filed on Nov. 30, 2018, provisional application No. 62/796,831, filed on Jan. 25, 2019, provisional application No. 62/800,287, filed on Feb. 1, 2019, provisional application No. 62/801,260, filed on Feb. 5, 2019, provisional application No. 62/813,335, filed on Mar. 4, 2019, provisional application No. 62/821,116, filed on Mar. 20, 2019, provisional application No. 62/836,357, filed on Apr. 19, 2019, provisional application No. 62/836,352, filed on Apr. 19, 2019, provisional application No. 62/843,796, filed on May 6, 2019, provisional application No. 62/878,364, filed on Jul. 25, 2019.

(51) Int. Cl.

| | | |
|---|---|---|
| *A61B 6/03* | (2006.01) | |
| *A61B 6/06* | (2006.01) | |
| *A61B 6/02* | (2006.01) | |
| *A61N 5/10* | (2006.01) | |
| *A61B 6/08* | (2006.01) | |
| *G06T 7/30* | (2017.01) | |
| *A61B 5/055* | (2006.01) | |
| *A61B 6/04* | (2006.01) | |

(52) U.S. Cl.
CPC ............ *A61B 6/405* (2013.01); *A61B 6/4078* (2013.01); *A61B 6/4085* (2013.01); *A61B 6/469* (2013.01); *A61B 6/488* (2013.01); *A61B 6/5205* (2013.01); *G06T 11/005* (2013.01); *A61B 5/055* (2013.01); *A61B 6/025* (2013.01); *A61B 6/03* (2013.01); *A61B 6/035* (2013.01); *A61B 6/0407* (2013.01); *A61B 6/08* (2013.01); *A61B 6/4014* (2013.01); *A61B 6/4021* (2013.01); *A61B 6/4028* (2013.01); *A61B 6/4064* (2013.01); *A61B 6/4435* (2013.01); *A61B 6/4441* (2013.01); *A61B 6/4458* (2013.01); *A61B 6/481* (2013.01); *A61B 6/482* (2013.01); *A61B 6/483* (2013.01); *A61B 6/484* (2013.01); *A61B 6/541* (2013.01); *A61B 6/582* (2013.01); *A61N 5/107* (2013.01); *A61N 5/1067* (2013.01); *A61N 5/1071* (2013.01); *A61N 5/1082* (2013.01); *A61N 2005/1085* (2013.01); *A61N 2005/1091* (2013.01); *A61N 2005/1095* (2013.01); *G06T 7/30* (2017.01); *G06T 11/008* (2013.01); *G06T 2207/10081* (2013.01); *G06T 2210/41* (2013.01); *G06T 2211/404* (2013.01); *G06T 2211/412* (2013.01); *G06T 2211/424* (2013.01); *G06T 2211/428* (2013.01); *G06T 2211/432* (2013.01)

(58) Field of Classification Search
CPC ....... A61B 6/06; A61B 6/4078; A61B 6/4085; A61B 6/488; A61N 5/1048; G06T 11/005
See application file for complete search history.

(56) References Cited

U.S. PATENT DOCUMENTS

| | | | |
|---|---|---|---|
| 6,233,478 B1 | 5/2001 | Liu | |
| 6,307,909 B1 | 10/2001 | Flohr et al. | |
| 7,050,528 B2 | 5/2006 | Chen | |
| 7,336,759 B2 * | 2/2008 | Nukui | A61B 6/5282 378/207 |
| 7,660,380 B2 | 2/2010 | Boese et al. | |
| 8,116,430 B1 | 2/2012 | Shapiro et al. | |
| 8,467,497 B2 | 6/2013 | Lu et al. | |
| 8,588,363 B2 | 11/2013 | Flohr | |
| 9,400,332 B2 | 7/2016 | Star-Lack et al. | |
| 2003/0076927 A1 | 4/2003 | Shigeyuki et al. | |
| 2004/0091079 A1 | 5/2004 | Zapalac | |
| 2004/0202360 A1 | 10/2004 | Besson | |
| 2005/0053188 A1 | 3/2005 | Gohno | |
| 2005/0251029 A1 | 11/2005 | Khamene et al. | |
| 2006/0109954 A1 | 5/2006 | Gohno | |
| 2006/0262894 A1 | 11/2006 | Bernhadt et al. | |
| 2007/0127621 A1 | 6/2007 | Grass et al. | |
| 2007/0189444 A1 | 8/2007 | Van Steven-Daal et al. | |
| 2008/0103834 A1 | 5/2008 | Reiner | |
| 2008/0112532 A1 | 5/2008 | Schlomka et al. | |
| 2009/0080603 A1 | 3/2009 | Shukla et al. | |
| 2009/0135994 A1 | 5/2009 | Yu et al. | |
| 2009/0161826 A1 | 6/2009 | Gertner et al. | |
| 2009/0225932 A1 | 9/2009 | Zhu et al. | |
| 2009/0283682 A1 | 11/2009 | Star-Lack et al. | |
| 2009/0304142 A1* | 12/2009 | Ruimi | A61B 6/4291 378/7 |
| 2010/0046819 A1 | 2/2010 | Noo et al. | |
| 2010/0208964 A1 | 8/2010 | Wiegert et al. | |
| 2011/0142312 A1 | 6/2011 | Toth et al. | |
| 2011/0255656 A1* | 10/2011 | Star-Lack | A61B 6/5282 378/7 |
| 2012/0014582 A1 | 1/2012 | Schaefer et al. | |
| 2012/0207370 A1* | 8/2012 | Fahimian | A61B 6/484 382/131 |
| 2012/0263360 A1* | 10/2012 | Zhu | G06T 5/002 382/131 |
| 2012/0294504 A1 | 11/2012 | Kyriakou | |
| 2013/0101082 A1 | 4/2013 | Jordan et al. | |
| 2013/0294570 A1 | 11/2013 | Hansis | |
| 2014/0018671 A1* | 1/2014 | Li | A61B 6/12 600/424 |
| 2014/0086383 A1 | 3/2014 | Huwer et al. | |
| 2014/0169652 A1 | 6/2014 | Vic et al. | |
| 2015/0297165 A1 | 10/2015 | Tanaka et al. | |
| 2015/0305696 A1 | 10/2015 | Yamakawa et al. | |
| 2016/0016009 A1 | 1/2016 | Manzke et al. | |
| 2016/0120486 A1 | 5/2016 | Goto et al. | |
| 2016/0220844 A1 | 8/2016 | Paysan et al. | |
| 2016/0262709 A1 | 9/2016 | Siewerdsen et al. | |
| 2017/0000428 A1 | 1/2017 | Goto | |
| 2017/0197098 A1 | 7/2017 | Hirasawa et al. | |
| 2017/0205360 A1 | 7/2017 | Cinquin et al. | |
| 2017/0332982 A1 | 11/2017 | Koehler et al. | |
| 2018/0070894 A1 | 3/2018 | Osaki et al. | |
| 2018/0192978 A1 | 7/2018 | Naylor | |
| 2018/0345042 A1 | 12/2018 | Voronenko et al. | |
| 2019/0099149 A1 | 4/2019 | Li | |
| 2020/0016432 A1 | 1/2020 | Maolinbay | |
| 2020/0121267 A1 | 4/2020 | Deutschmann | |
| 2020/0402644 A1 | 12/2020 | Zhou et al. | |
| 2021/0165122 A1 | 6/2021 | Morton | |

FOREIGN PATENT DOCUMENTS

| | | |
|---|---|---|
| EP | 2383702 A1 | 11/2011 |
| JP | H09 218939 A | 8/1997 |
| JP | 2004 136021 | 5/2004 |
| JP | 2008 036275 | 2/2008 |
| WO | 2005112753 A2 | 12/2005 |
| WO | 2006/078386 A2 | 7/2006 |
| WO | 2010/014288 A1 | 2/2010 |
| WO | 2010/099621 A1 | 9/2010 |
| WO | 2015103184 A1 | 7/2015 |
| WO | 2018/156968 A1 | 8/2018 |
| WO | 2018/183748 A1 | 10/2018 |

OTHER PUBLICATIONS

International Search Report and Written Opinion from PCT/US2019/063071 dated Mar. 18, 2020.

International Search Report and Written Opinion from PCT/US2019/063073 dated Apr. 3, 2020.

International Search Report and Written Opinion from PCT/US2019/063078 dated Oct. 8, 2020.

(56) References Cited

OTHER PUBLICATIONS

International Search Report and Written Opinion from PCT/US2019/063083 dated Mar. 16, 2020.
International Search Report and Written Opinion from PCT/US2019/063085 dated Mar. 16, 2020.
Invitation to Pay Additional Fees from PCT/US2019/063086 dated Mar. 26, 2020.
International Search Report and Written Opinion from PCT/US2019/063087 dated Apr. 3, 2020.
International Search Report and Written Opinion from PCT/US2019/063077 dated Mar. 16, 2020.
International Search Report and Written Opinion from PCT/US2019/063076 dated Mar. 16, 2020.
International Search Report and Written Opinion from PCT/US2019/063074 dated Mar. 23, 2020.
International Search Report and Written Opinion from PCT/US2019/063086 dated Nov. 16, 2020.
Kang et al., "Accurate for Head and Neck Cancer Patients Using 2D and 3D Image Guidance", Journal of Applied Clinical Medical Physics, vol. 12, No. 1, Dec. 1, 2011, pp. 86-96, XP055734549.
Ramamurthi et al., "Region of Interest Cone Beam Tomography With Prior CT Data," Conference Record of the 37th Asilomar Conference on Signals, Systems, & Computers, vol. 2, Nov. 9, 2003, pp. 1924-1927.
Spearman, et al. Effect of Automated Attenuation-Based Tube Voltage Selection on Radiation Dose at CT: An Observational Study on a Global Scale11 , Radiology, vol. 279, No. Apr. 1, 2016 (Apr. 1, 2016), pp. 167-174, XP055734550.
Vinson et al., "X-Ray Micro-CT With a Displaced Detector Array: Application to Helical Cone-Beam Reconstruction," Medical Physics, vol. 30, No. 10, Oct. 1, 2003, pp. 2758-2761.
Wang et al., "A General Cone-Beam Reconstruction Algorithm," IEEE Transactions on Medical Imaging, vol. 12, No. 3, Sep. 1, 1993.
Wang, "X-Ray Micro-CT With a Displaced Detector Array," Medical Physics, vol. 29, No. 7, Jul. 1, 2002.
Office Action from U.S. Appl. No. 16/694,145 dated Mar. 17, 2021, 10 pages.
Office Action from U.S. Appl. No. 16/694,190 dated Mar. 26, 2021, 9 pages.
Notice of Allowance from U.S. Appl. No. 16/694,190 dated Jun. 23, 2021, 8 pages.
Office Action from U.S. Appl. No. 16/694,192 dated Jun. 10, 2021, 10 pages.
Office Action from U.S. Appl. No. 16/694,202 dated Apr. 9, 2021, 12 pages.
Restriction Requirement from U.S. Appl. No. 16/694,210 dated Jun. 10, 2021, 6 pages.
Office Action from U.S. Appl. No. 16/694,230 dated Apr. 1, 2021, 6 pages.
Clackdoyle, et al., Data consistency conditions for truncated fanbeam and parallel projections, Med. Phys. Feb. 2015, pp. 831-845, vol. 42, No. 2.
Defrise, et al., A solution to the long-object problem in helical cone-beam tomography, Physics in Medicine and Biology, 2000, pp. 623-643, vol. 45.
Hsieh, et al., A novel reconstruction algorithm to extend the CT scan field-of-view, Med. Phys., Sep. 2004, pp. 2385-2391, vol. 31, No. 9.
Katsevich, A., An improved exact filtered backprojection algorithm for spiral computed tomography, Advances in Applied Mathematics, 2004, pp. 691-697, vol. 32.
Kudo et al., Exact and approximate algorithms for helical cone-beam CT, Physics in Medicine and Biology, 2004, pp. 1-26, vol. 49, No. 13.
Kunze, et al., Cone beam reconstruction with displaced flat panel detector, 10th International Meeting on Fully Three-Dimensional Image Reconstruction in Radiology and Nuclear Medicine, 2009, pp. 138-141.
Li et al., Scatter kernel estimation with an edge-spread function method for cone-beam computed tomography imaging, Physics in Medicine and Biology, pp. 6729-6748, vol. 51.
Maslowski, et al., Acuros CTS: A fast, linear Boltzmann transport equation solver for computed tomography scatter—Part I: Core algorithms and validation, Med. Phys., 2018, pp. 1-15.
Ning, et al., X-ray scatter correction algorithm for cone beam CT imaging, Med. Phys., May 2004, pp. 1195-1202, vol. 31, No. 5.
Noo et al., A new scheme for view-dependent data differentiation in fan-beam and cone-beam computed tomography, Physics in Medicine and Biology, 2007, pp. 5593-5414, vol. 52.
Schäfer, et al., FBP and BPF reconstruction methods for circular X-ray tomography with off-center detector, Med. Phys., Jul. 2011, pp. S85-S94, vol. 38, No. 7.
Schäfer, et al., Cone-beam filtered back-projection for circular X-ray tomography with off-center detector, 10th International Meeting on Fully Three-Dimensional Image Reconstruction in Radiology and Nuclear Medicine, 2009, pp. 86-89.
Siewerdsen, et al., A simple, direct method for x-ray scatter estimation and correction in digital radiography and cone-beam CT, Med. Phys., Jan. 2006, pp. 187-197, vol. 33, No. 1.
Sun, et al., Improved scatter correction using adaptive scatter kernel superposition, Physics in Medicine and Biology, Oct. 2010, pp. 6695-6720, vol. 55.
Tang, et al., A sinogram extrapolation method for CT field of view extension, Proceedings of the Fifth CT Meeting, 2018, pp. 206-209.
Yu, et al., Radiation dose reduction in computed tomography: techniques and future perspective, Imaging Med., Oct. 2009, pp. 65-84, vol. 1.
Zamyatin, et al., Helical cone beam CT with an asymmetrical detector, Medical Physics, Oct. 2005, pp. 3117-3127, vol. 32, No. 10.
Zbijewski, et al., Efficient Monte Carlo Based Scatter Artifact Reduction in Cone-Beam Micro-CT, IEEE Transactions on Medical Imaging, Jul. 2006, pp. 817-827, vol. 25, No. 7.
Zhu, et al., Scatter Correction Method for X-ray CT Using Primary Modulation: Theory and Preliminary Results, IEEE Transactions on Medical Imaging, Dec. 2006, pp. 1573-1587, vol. 25, No. 12.
Zhu, et al. Noise suppression in scatter correction for cone-beam CT, American Association of Physicists in Medicine, 2009, pp. 741-752, vol. 36, No. 3.
Office Action from U.S. Appl. No. 16/694,161 dated Sep. 13, 2021, 18 pages.

* cited by examiner

METHOD AND APPARATUS FOR IMPROVING SCATTER ESTIMATION AND CORRECTION IN IMAGING

CROSS-REFERENCE TO RELATED APPLICATIONS

This application claims the benefit of eleven U.S. provisional patent applications, including Ser. No. 62/773,712, filed Nov. 30, 2018; Ser. No. 62/773,700, filed Nov. 30, 2018; Ser. No. 62/796,831, filed Jan. 25, 2019; Ser. No. 62/800,287, filed Feb. 1, 2019; Ser. No. 62/801,260, filed Feb. 5, 2019; Ser. No. 62/813,335, filed Mar. 4, 2019; Ser. No. 62/821,116, filed Mar. 20, 2019; Ser. No. 62/836,357, filed Apr. 19, 2019; Ser. No. 62/836,352, filed Apr. 19, 2019; Ser. No. 62/843,796, filed May 6, 2019; and Ser. No. 62/878,364, filed Jul. 25, 2019. This application is also related to ten non-provisional U.S. patent applications filed on the same day, including, entitled "MULTIMODAL RADIATION APPARATUS AND METHODS;", entitled "APPARATUS AND METHODS FOR SCALABLE FIELD OF VIEW IMAGING USING A MULTI-SOURCE SYSTEM;", entitled "INTEGRATED HELICAL FAN-BEAM COMPUTED TOMOGRAPHY IN IMAGE-GUIDED RADIATION TREATMENT DEVICE;", entitled "COMPUTED TOMOGRAPHY SYSTEM AND METHOD FOR IMAGE IMPROVEMENT USING PRIOR IMAGE;", entitled "OPTIMIZED SCANNING METHODS AND TOMOGRAPHY SYSTEM USING REGION OF INTEREST DATA;", entitled "HELICAL CONE-BEAM COMPUTED TOMOGRAPHY IMAGING WITH AN OFF-CENTERED DETECTOR;", entitled "MULTI-PASS COMPUTED TOMOGRAPHY SCANS FOR IMPROVED WORKFLOW AND PERFORMANCE;", entitled "METHOD AND APPARATUS FOR SCATTER ESTIMATION IN CONE-BEAM COMPUTED TOMOGRAPHY;", entitled "ASYMMETRIC SCATTER FITTING FOR OPTIMAL PANEL READOUT IN CONE-BEAM COMPUTED TOMOGRAPHY;" and, entitled "METHOD AND APPARATUS FOR IMAGE RECONSTRUCTION AND CORRECTION USING INTER-FRACTIONAL INFORMATION." The contents of all above-identified patent application(s) and patent(s) are fully incorporated herein by reference.

FIELD OF THE INVENTION

Aspects of the disclosed technology relate to estimating scatter in projection data, and, more particularly, to utilizing a narrow aperture scan to estimate scatter in a wider aperture scan during various imaging techniques, including x-ray, computed tomography (CT), and cone-beam computed tomography (CBCT) scans.

BACKGROUND

Scatter in cone-beam CT can account for a significant portion of the detected photons, especially when no anti-scatter grids are used with a wide collimation opening. Scatter can negatively impact image quality, including contrast and quantitative accuracy. Consequently, scatter measurement, estimation, and correction are applicable to cone-beam CT data processing and image reconstruction, including in the context of image-guided radiation treatment (IGRT). IGRT can make use of medical imaging technology, such as CT, to collect images of a patient before, during, and/or after treatment.

For cone-beam computed tomography (CBCT) using flat panels, a pair of high attenuation blades as part of a collimator can be used to form an aperture that limits the axial range that the x-ray beam illuminates in the patient/panel. A large aperture allows for a large axial coverage of the patient during the scan. Hence, by using a wider aperture, the total scanning time can be reduced if a large axial range of the patient needs to be imaged. The tradeoff, however, is that the amount of scatter also increases with the aperture, while the primary data stays the same. Without scatter correction, the increased scatter will negatively impact the image quality and quantitation.

Hardware-based scatter reduction includes the use of anti-scatter grids on the detector panel surface, the use of very narrow apertures, bow-tie filters, air separation between patient and detector, etc. A conventional anti-scatter grid can reduce the amount of x-ray scatter significantly. The main drawbacks are that the system is more complex, and a significant amount of primary data is also reduced. Using a very narrow aperture, the scatter can be reduced significantly (and to effectively a negligible level), however, the axial coverage is so small that the overall scanning time becomes impractical.

Software-based scatter reduction/correction can use physical models to estimate the scatter in the acquired data. These methods can model both a data acquisition system and the interaction process between x-rays and materials. The former requires detailed knowledge of the major components of the entire imaging chain as well as information of the patient, which may be obtained from a planning CT or a first-pass reconstruction without scatter correction. These methods can either be realized stochastically (e.g., Monte-Carlo-simulation based approaches) or deterministically (e.g., radiative-transfer-equation based approaches). The former is computationally costly, and the latter is generally considered as an open problem in the field. Model-based methods are typically patient specific and can be more accurate. However, these methods require a considerable amount of prior information on the data acquisition system and the patient, such that the effectiveness of these methods is highly dependent on the modeling accuracy. Furthermore, they are also highly demanding in terms of computational power and time resulting in a significant negative impact on workflow and throughput. The estimated scatter is then used to correct the data prior to image reconstruction or during image reconstruction.

Among software-based scatter correction approaches is kernel-based scatter estimation and correction. In the kernel-based approaches, a scatter kernel is determined through physical measurements or Monte Carlo simulation assuming a composite of materials. For example, one typical technique measures the scatter kernels with different thicknesses of water layers at given x-ray spectrum and apertures. The apertures, projected to the detector plane, can be as large as the panel's axial dimension. Once the kernels at different water layers are measured/determined, they are used for scatter correction in patient scans, assuming that the patient tissues are equivalent to the different thickness layers of water. The application of the kernels for scatter estimation and correction can include scatter deconvolution using the kernels, either in the space domain or in the frequency domain, and can be adaptive to local variation of the object. For example, measured scatter data can be considered a convolution result of the primary and the scatter kernels. A deconvolution process can be performed to separate the primary and scatter by using the appropriate kernels that are established ahead of time.

Kernel-based scatter estimation/correction is widely used for CBCT due to its simplicity. A fundamental challenge of this type of approach, however, is that the accuracy can degrade when the patient tissue distribution is highly non-uniform, especially in chest and pelvic regions. Furthermore, when the aperture size is large, the performance of the approach can also degrade based on the elevated scatter associated with the large aperture.

BRIEF SUMMARY

In one embodiment, an imaging apparatus includes a rotating imaging source for emitting a radiation beam, a detector positioned to receive radiation from the imaging source, and a beamformer configured to adjust a shape of the radiation beam emitted by the imaging source, such that the shape of the radiation beam is configured for a wide aperture scan of a wide axial region and a narrow aperture scan of a narrow axial region within the wide axial region, where an estimated scatter in the wide axial region is based on the projection data from the narrow axial region.

Features that are described and/or illustrated with respect to one embodiment may be used in the same way or in a similar way in one or more other embodiments and/or in combination with or instead of the features of the other embodiments.

The descriptions of the invention do not limit the words used in the claims in any way or the scope of the claims or invention. The words used in the claims have all of their full ordinary meanings.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify embodiments of this invention. It will be appreciated that illustrated element boundaries (e.g., boxes, groups of boxes, or other shapes) in the figures represent one embodiment of boundaries. In some embodiments, one element may be designed as multiple elements or that multiple elements may be designed as one element. In some embodiments, an element shown as an internal component of another element may be implemented as an external component and vice versa. Furthermore, elements may not be drawn to scale.

DETAILED DESCRIPTION

Figure 1:
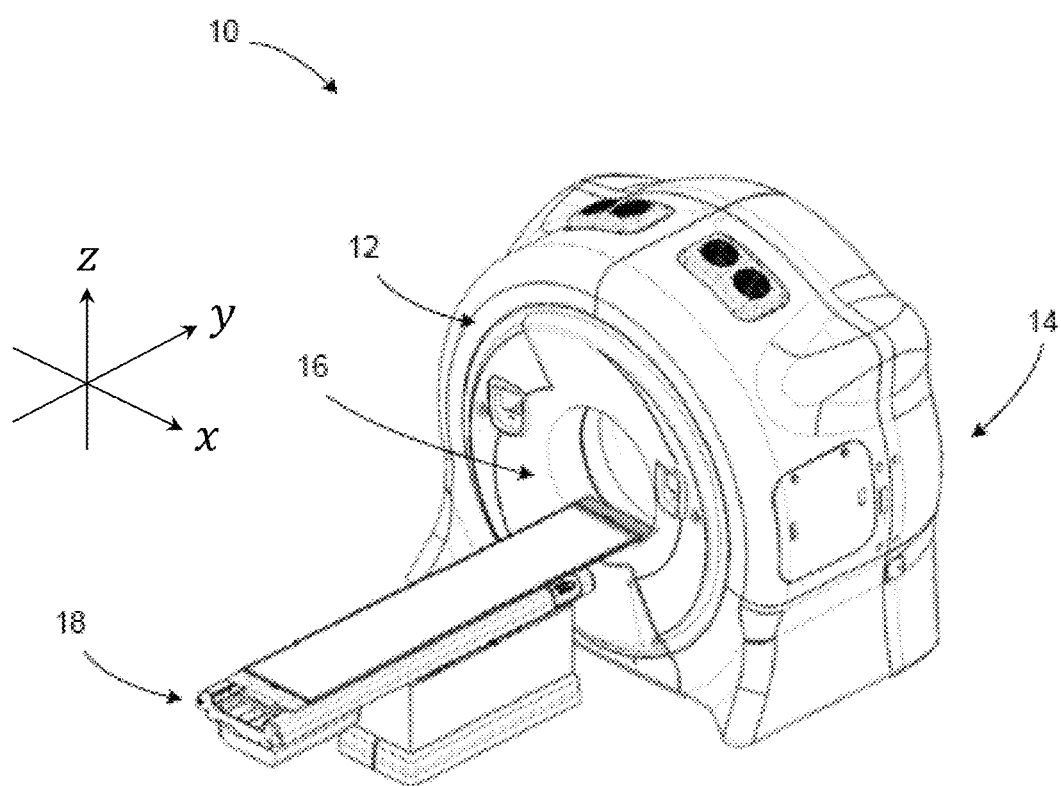
FIG. 1 is a perspective view of an exemplary x-ray imaging apparatus in accordance with one aspect of the disclosed technology.

The following includes definitions of exemplary terms that may be used throughout the disclosure. Both singular and plural forms of all terms fall within each meaning.

"Component," as used herein can be defined as a portion of hardware, a portion of software, or a combination thereof. A portion of hardware can include at least a processor and a portion of memory, wherein the memory includes an instruction to execute. A component may be associated with a device.

"Logic," synonymous with "circuit" as used herein, includes but is not limited to hardware, firmware, software and/or combinations of each to perform a function(s) or an action(s). For example, based on a desired application or needs, logic may include a software-controlled microprocessor, discrete logic such as an application specific integrated circuit (ASIC), or other programmed logic device and/or controller. Logic may also be fully embodied as software.

"Processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read-only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

"Signal," as used herein includes, but is not limited to, one or more electrical signals, including analog or digital signals, one or more computer instructions, a bit or bit stream, or the like.

"Software", as used herein, includes but is not limited to one or more computer readable and/or executable instructions that cause a computer, processor, logic, and/or other electronic device to perform functions, actions, and/or behave in a desired manner. The instructions may be embodied in various forms such as routines, algorithms, modules, or programs including separate applications or code from dynamically linked sources or libraries.

While the above exemplary definitions have been provided, it is Applicant's intention that the broadest reasonable interpretation consistent with this specification be used for these and other terms.

As is discussed in more detail below, embodiments of the disclosed technology relate to estimating scatter in imaging projection data, including utilizing data from a narrow aperture scan within a wider aperture scan to estimate scatter in data from the wider aperture scan, during x-ray, CT, and CBCT scans. In some embodiments, a radiotherapy delivery device and method can make use of an integrated low-energy radiation source for CT for use in conjunction with or as part of IGRT. In particular, for example, a radiotherapy delivery device and method can combine a low-energy collimated radiation source for imaging in a gantry using rotational (e.g., helical or step-and-shoot) image acquisition along with a high-energy radiation source for therapeutic treatment.

The low-energy radiation source (e.g., kilovolt (kV)) can produce higher quality images than via use of the high-energy radiation source (e.g., megavolt (MV)) for imaging. Images generated with kV energy typically have better tissue contrast than with MV energy. High quality volume imaging can be needed for visualization of targets and organs-at-risk (OARS), for adaptive therapy monitoring, and for treatment planning/re-planning. In some embodiments, the kV imaging system can also be used for positioning, motion tracking, and/or characterization or correction capabilities.

The image acquisition methodology can include or otherwise make use of a multiple rotation scan, which may be, for example, a continuous scan (e.g., with a helical source trajectory about a central axis together with longitudinal movement of a patient support through a gantry bore), a non-continuous circular stop-and-reverse scan with incremental longitudinal movement of a patient support, step-and-shoot circular scans, etc.

In accordance with various embodiments, the imaging apparatus collimates a radiation source, including, for example, into a cone beam or a fan beam using, for example, a beamformer. In one embodiment, the collimated beam can be combined with a gantry that continuously rotates while the patient moves, resulting in a helical image acquisition.

In some embodiments, the time associated with increased scanning rotations to complete a high-quality volume image may be mitigated by high gantry rates/speed (e.g., using fast slip ring rotation, including, e.g., up to 10 revolutions per minute (rpm), up to 20 rpm, up to 60 rpm, or more rpm), high kV frame rates, and/or sparse data reconstruction techniques, to provide kV CT imaging on a radiation therapy delivery platform. Detectors (with various row/slice sizes, configurations, dynamic range, etc.), scan pitch, and/or dynamic collimation are additional features in various embodiments, including to selectively expose portions of the detector and selectively define active readout areas, as discussed in detail below. In particular, image quality can be improved (by estimating the scatter as described below) by using an adjustable beamformer/collimator on the x-ray (low-energy) imaging radiation source and/or optimizing the detector readout range.

The imaging apparatus and method can provide selective and variable collimation of a radiation beam emitted by the source of radiation, including adjusting the radiation beam shape to expose less than the entire active area of an associated radiation detector (e.g., a radiation detector positioned to receive radiation from the x-ray radiation source). For example, a beamformer of the imaging apparatus can adjust the shape of the radiation beam as the pitch varies during a helical scan. In another example, the beam aperture can be adjusted by the beamformer for various axial field-of-view (aFOV) requirements. In particular, the aFOV can be adjusted for scanning regions with various axial (longitudinal) lengths, including narrow regions and wide regions. Also, exposing only a primary region of the detector to direct radiation allows shadowed regions of the detector to receive only scatter. In some embodiments, scatter measurements in the shadow region (and in some embodiments measurements in the penumbra region) of the detector can be used to estimate scatter in the primary region of the detector receiving projection data.

The imaging apparatus and method can provide selective and variable detector readout areas and ranges, including adjusting the detector readout range to limit the active area of the detector for improved readout speed. For example, less than the available shadow region data may be read and used for scatter estimation. Combining selective readout with beamforming allows for various optimizations of scatter fitting techniques.

Figure 2:
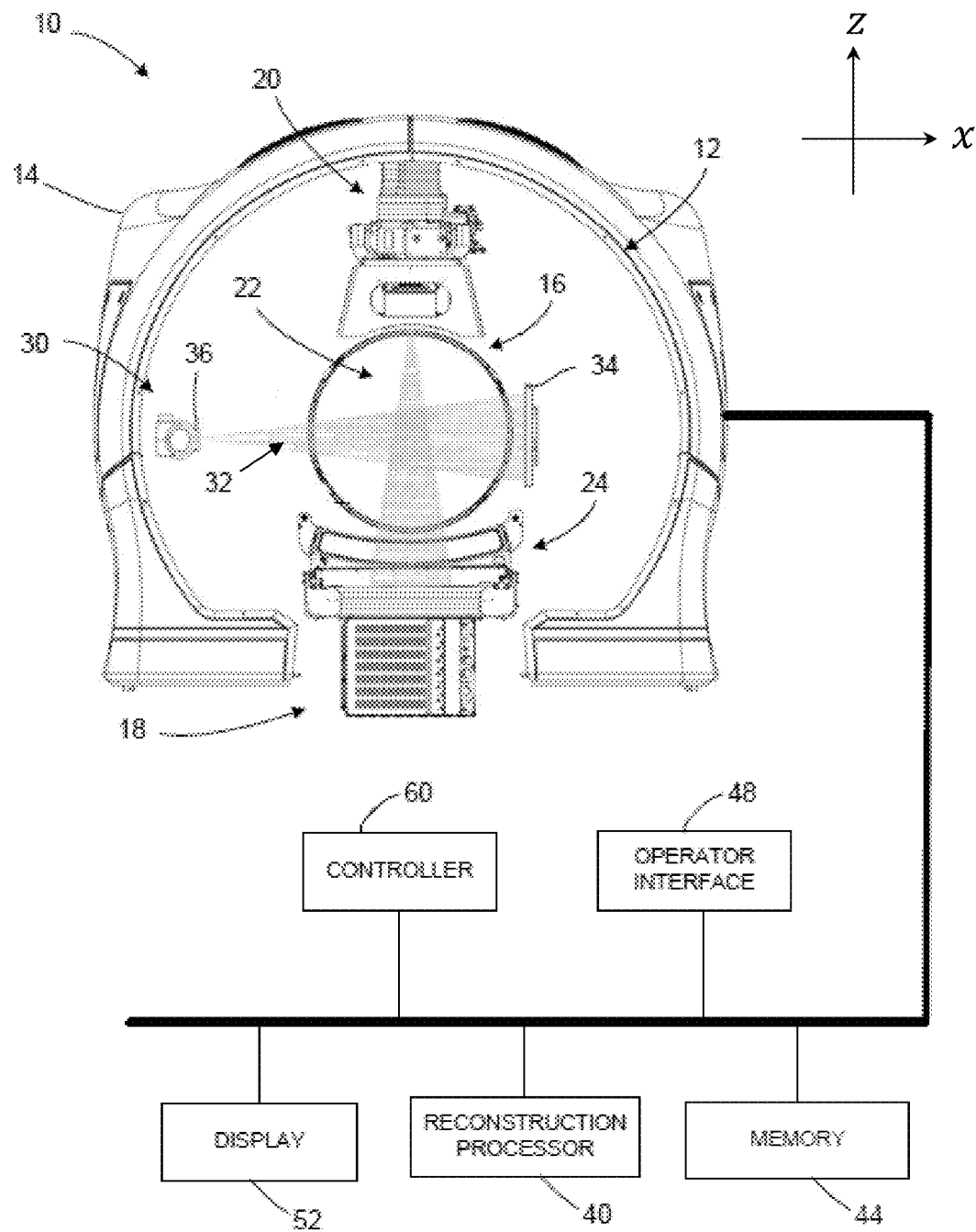
FIG. 2 is a diagrammatic illustration of an x-ray imaging apparatus integrated into an exemplary radiotherapy device in accordance with one aspect of the disclosed technology.

With reference to FIG. 1 and FIG. 2, an imaging apparatus 10 (e.g., an x-ray imaging apparatus) is shown. It will be appreciated that the imaging apparatus 10 may be associated with and/or integrated into a radiotherapy device (as shown in FIG. 2) that can be used for a variety of applications, including, but not limited to IGRT. The imaging apparatus 10 includes a rotatable gantry system, referred to as gantry 12 supported by or otherwise housed in a support unit or housing 14. Gantry herein refers to a gantry system that comprises one or more gantries (e.g., ring or C-arm) capable of supporting one or more radiation sources and/or associated detectors as they rotate around a target. For example, in one embodiment, a first radiation source and its associated detector may be mounted to a first gantry of the gantry system and a second radiation source and its associated detector may be mounted to a second gantry of the gantry system. In another embodiment, more than one radiation source and associated detector(s) may be mounted to the same gantry of the gantry system, including, for example, where the gantry system is comprised of only one gantry. Various combinations of gantries, radiation sources, and radiation detectors may be combined into a variety of gantry system configurations to image and/or treat the same volume within the same apparatus. For example, kV and MV radiation sources can be mounted on the same or different gantries of the gantry system and selectively used for imaging and/or treatment as part of an IGRT system. If mounted to different gantries, the radiation sources are able to rotate independently, but are still able to simultaneously image the same (or nearly the same) volume. A rotatable ring gantry 12 may be capable of 10 rpm or more, as mentioned above. The rotatable gantry 12 defines a gantry bore 16 into and through which a patient can be moved and positioned for imaging and/or treatment. In accordance with one embodiment, the rotatable gantry 12 is configured as a slip ring gantry to provide continuous rotation of an imaging radiation source (x-ray) and an associated radiation detector while providing sufficient bandwidth for the high-quality imaging data received by the detector. A slip-ring gantry can eliminate gantry rotations in alternating directions in order to wind and unwind cables carrying the power and signals associated with the device. Such a configuration will allow for continuous helical computed tomography, including CBCT, even when integrated into an IGRT system.

A patient support 18 is positioned adjacent to the rotatable gantry 12 and configured to support a patient, typically in a horizontal position, for longitudinal movement into and within the rotatable gantry 12. The patient support 18 can move the patient, for example, in a direction perpendicular to the plane of rotation of the gantry 12 (along or parallel to the rotation axis of the gantry 12). The patient support 18 can be operatively coupled to a patient support controller for controlling movement of the patient and patient support 18. The patient support controller can be synchronized with the rotatable gantry 12 and sources of radiation mounted to the rotating gantry for rotation about a patient longitudinal axis in accordance with a commanded imaging and/or treatment plan. The patient support can also be moved in a limited range up and down, left and right once it is in the bore 16 to adjust the patient position for optimal treatment. Axes x, y, and z are shown, where, viewing from the front of the gantry 12, the x-axis is horizontal and points to the right, the y-axis points into the gantry plane, and the z-axis is vertical and points to the top. The x-, y-, and z-axes follow the right-hand rule.

It will be appreciated that other variations can be employed without departing from the scope of the disclosed technology. For example, the rotatable gantry 12 and patient support 18 can be controlled such that the gantry 12 rotates in a "back-and-forth" manner (e.g., alternating clockwise rotation and counterclockwise rotation) around a patient supported on the patient support (as opposed to continuously, as is described above) as the support is controlled to move (at a constant or variable speed) relative to the rotatable gantry 12. In another embodiment, with successive step-and-shoot circular scans, movement of the patient support 18 in the longitudinal direction (step) alternates with a scanning revolution by the rotatable gantry 12 (shoot) until the desired volume is captured. The device 10 is capable of volume-based and planar-based imaging acquisitions. For example, in various embodiments, the device 10 may be used to acquire volume images and/or planar images and execute the associated processing methods described below.

Various other types of radiation source and/or patient support movement may be utilized to achieve relative motion of the radiation source and the patient for generation of projection data. Non-continuous motion of the radiation source and/or patient support, continuous but variable/non-constant (including linear and non-linear) linear movement, speed, and/or trajectories, etc., and combinations thereof may be used, including in combination with the various embodiments of radiotherapy devices 10 described above.

As shown in FIG. 2, the x-ray imaging apparatus 10 includes a source of imaging radiation 30 coupled to or otherwise supported by the rotatable gantry 12. The source of imaging radiation 30 emits a radiation beam (indicated generally as 32) for generating high-quality images. In this embodiment, the source of imaging radiation is an x-ray source 30, configured as a kilovoltage (kV) source (e.g., a clinical x-ray source having an energy level in the range of about 20 kV to about 150 kV). In one embodiment, the kV source of radiation comprises a kilo-electron volt peak photon energy (keV) up to 150 keV. The imaging radiation source can be any type of transmission source suitable for imaging. For example, the imaging radiation source may be, for example, an x-ray generating source (including for CT) or any other way to produce photons with sufficient energy and flux (such as, e.g., a gamma-source (e.g., Cobalt-57, energy peak at 122 keV), an x-ray fluorescence source (such as fluorescence source through Pb k lines, two peaks @about 70 keV and @about 82 keV), etc.). References herein to x-ray, x-ray imaging, x-ray imaging source, etc. are exemplary for particular embodiments. Other imaging transmission sources can be used interchangeably in various other embodiments.

The x-ray imaging apparatus 10 also can include another source of radiation 20 coupled to or otherwise supported by the rotatable gantry 12. In accordance with one embodiment, the source of radiation 20 is configured as a source of therapeutic radiation, such as a high-energy source of radiation used for treatment of a tumor within a patient in a region of interest. It will be appreciated that the source of therapeutic radiation can be a high-energy x-ray beam (e.g., megavoltage (MV) x-ray beam), and/or a high-energy particle beam (e.g., a beam of electrons, a beam of protons, or a beam of heavier ions, such as carbon) or another suitable form of high-energy radiation without departing from the scope of the disclosed technology. In one embodiment, the source of radiation 20 comprises a mega-electron volt peak photon energy (MeV) of 1 MeV or greater. In one embodiment, the high-energy x-ray beam has an average energy greater than 0.8 MeV. In another embodiment, the high-energy x-ray beam has an average energy greater than 0.2 MeV. In another embodiment, the high-energy x-ray beam has an average energy greater than 150 keV. Generally, the source of radiation 20 has a higher energy level (peak and/or average, etc.) than the source of imaging radiation 30.

In one embodiment, the source of radiation 20 is a LINAC producing therapeutic radiation (e.g., MV) and the imaging system comprises an independent source of imaging radiation 30 producing relatively low intensity and lower energy imaging radiation (e.g., kV). In other embodiments, the source of radiation 20 could be a radioisotope, such as, for example, Co-60, which can generally have energy >1 MeV. The source of radiation 20 can emit one or more beams of radiation (indicated generally by 22) toward a region-of-interest (ROI) within a patient supported on the patient support 18 in accordance with a treatment plan.

In some embodiments, sources of radiation 20, 30 may be used in conjunction with one another to provide higher quality and better utilized images. In other embodiments, at least one additional radiation source can be coupled to the rotatable gantry 12 and operated to acquire projection data at a peak photon energy distinct from the peak photon energies of sources of radiation 20, 30.

Although FIGS. 1 and 2 depict an x-ray imaging apparatus 10 with a radiation source 30 mounted to a ring gantry 12, other embodiments may include other types of rotatable imaging apparatuses, including, for example, C-arm gantries and robotic arm-based systems. In gantry-based systems, a gantry rotates the imaging radiation source 30 around an axis passing through the isocenter. Gantry-based systems include C-arm gantries, in which the imaging radiation source 30 is mounted, in a cantilever-like manner, over and rotates about the axis passing through the isocenter. Gantry-based systems further include ring gantries, for example, rotatable gantry 12, having generally toroidal shapes in which the patient's body extends through a bore of the ring/toroid, and the imaging radiation source 30 is mounted on the perimeter of the ring and rotates about the axis passing through the isocenter. In some embodiments, the gantry 12 rotates continuously. In other embodiments, the gantry 12 utilizes a cable-based system that rotates and reverses repeatedly.

A detector 34 (e.g., two-dimensional flat detector or curved detector) can be coupled to or otherwise supported by the rotatable gantry 12. The detector 34 (e.g., x-ray detector) is positioned to receive radiation from the x-ray source 30 and can rotate along with the x-ray source 30. The detector 34 can detect or otherwise measure the amount of radiation not attenuated and therefore infer what was in fact attenuated by the patient or associated patient ROI (by comparison to what was initially generated). The detector 34 can detect or otherwise collect attenuation data from different angles as the radiation source 30 rotates around and emits radiation toward the patient.

It will be appreciated that the detector 34 can take on a number of configurations without departing from the scope of the disclosed technology. As illustrated in FIG. 2, the detector 34 can be configured as a flat-panel detector (e.g., a multi-row flat panel detector). In accordance with another exemplary embodiment, the detector 34 can be configured as a curved detector.

A collimator or beamformer assembly (indicated generally as 36) is positioned relative to the imaging (x-ray) source 30 to selectively control and adjust a shape of a radiation beam 32 emitted by the x-ray source 30 to selectively expose a portion or region of the active area of the detector 34. The beamformer can also control how the radiation beam 32 is positioned on the detector 34. In one embodiment, the beamformer 36 could have one degree/dimension of motion (e.g., to make a thinner or fatter slit). In another embodiment, the beamformer 36 can have two degrees/dimensions of motion (e.g., to make various sized rectangles). In other embodiments, the beamformer 36 may be capable of various other dynamically-controlled shapes, including, for example, parallelograms. All of these shapes may be dynamically adjusted during a scan. In some embodiments, blocking portions of the beamformer can be rotated and translated.

The beamformer 36 can be controlled to adjust the shape of the radiation beam 32 emitted by the x-ray source 30 dynamically in a number of geometries, including, but not limited to, a fan beam or cone beam having a beam thickness (width) as low as one detector row width or including multiple detector rows, which will be only a portion of the detector's active area. In various embodiments, the thickness of the beam may expose several centimeters of a larger detector active area. For example, 3-4 centimeters (measured in the longitudinal direction in the detector plane) of a 5-6 centimeter detector may be selectively exposed to the imaging radiation 32. In this embodiment, 3-4 centimeters of projection image data may be captured with each readout, with about 1-2 centimeters of unexposed detector area on one or each side, which may be used to capture scatter data, as discussed below.

In other embodiments, more or less of a portion of the active detector may be selectively exposed to the imaging radiation. For example, in some embodiments, the beam thickness may be reduced down to about two centimeters, one centimeter, less than one centimeter, or ranges of similar sizes, including with smaller detectors. In other embodiments, the beam thickness may be increased to about 4 centimeters, 5 centimeters, greater than 5 centimeters, or ranges of similar sizes, including with larger detectors. In various embodiments, the ratio of exposed-to-active detector area may be 30-90% or 50-75%. In other embodiments, the ratio of exposed-to-active detector area may be 60-70%. However, various other exposed and active area sizes or ratios of exposed-to-active detector area may be suitable in other embodiments. The beam and detector can be configured so that the shadowed region of the detector (active but not exposed to direct radiation) is sufficient to capture scatter data beyond the penumbra region.

Various embodiments may include an optimization of the features that control selective exposure of the detector (e.g., beam size, beam/aperture center, collimation, pitch, detector readout range, detector readout center, etc.) such that the measured data is sufficient for primary (exposed) and shadowed regions, but also optimized for speed and dosage control. The beamformer 36 shape/position and detector 34 readout range can be controlled such that the radiation beam 32 from the x-ray source 30 covers as much or as little of the x-ray detector 34 based on the particular imaging task and scatter estimation process being carried out, including, for example, combinations of narrow and wide aFOV scans.

The beamformer may be configured in a variety of ways that allow it to adjust the shape of the radiation beam 32 emitted by the x-ray source 30. For example, the collimator 36 can be configured to include a set of jaws or other suitable members that define and selectively adjust the size of an aperture through which the radiation beam from the x-ray source 30 may pass in a collimated manner. In accordance with one exemplary configuration, the collimator 36 can include an upper jaw and a lower jaw, where the upper and lower jaws are movable in different directions (e.g., parallel directions) to adjust the size of the aperture through which the radiation beam from the x-ray source 30 passes, and also to adjust the beam position relative to the patient to illuminate only the portion of the patient to be imaged for optimized imaging and minimized patient dose. For example, a collimator can be configured as a multi-leaf collimator (MLC), which can include a plurality of interlaced leaves operable to move to one or more positions between a minimally-open or closed position and a maximally-open position. It will be appreciated that the leaves can be moved into desired positions to achieve a desired shape of a radiation beam being emitted by the radiation source. In one embodiment, the MLC is capable of sub-millimeter targeting precision.

In accordance with one embodiment, the shape of the radiation beam 32 from the x-ray source 30 can be changed during an image acquisition. Stated differently, in accordance with one exemplary implementation, the beamformer 36 leaf positions and/or aperture width can be adjusted before or during a scan. For example, in accordance with one embodiment, the beamformer 36 can be selectively controlled and dynamically adjusted during rotation of the x-ray source 30 such that the radiation beam 32 has a shape with sufficient primary/shadow regions and is adjusted to include only an object of interest during imaging (e.g., the prostate). The shape of the radiation beam 32 being emitted by the x-ray source 30 can be changed during or after a scan, depending on the desired image acquisition, which may be based on imaging and/or therapeutic feedback, as discussed in more detail below.

Detector 24 can be coupled to or otherwise supported by the rotatable gantry 12 and positioned to receive radiation 22 from the therapeutic radiation source 20. The detector 24 can detect or otherwise measure the amount of radiation not attenuated and therefore infer what was in fact attenuated by the patient or associated patient ROI (by comparison to what was initially generated). The detector 24 can detect or otherwise collect attenuation data from different angles as the therapeutic radiation source 20 rotates around and emits radiation toward the patient.

It will be further appreciated that the therapeutic radiation source 20 can include or otherwise be associated with a beamformer or collimator. The collimator/beamformer associated with the therapeutic radiation source 20 can be configured in a number of ways, similar to the collimator/beamformer 36 associated with the imaging source 30.

The therapeutic radiation source 20 may be mounted, configured, and/or moved into the same plane or a different plane (offset) than the imaging source 30. In some embodiments, scatter caused by simultaneous activation of the radiation sources 20, 30 may be reduced by offsetting the radiation planes.

When integrated with a radiotherapy device, imaging apparatus 10 can provide images that are used to set up (e.g., align and/or register), plan, and/or guide a radiation delivery procedure (treatment). Typical set-up is accomplished by comparing current (in-treatment) images to pre-treatment image information. Pre-treatment image information may comprise, for example, x-ray, CT data, CBCT data, magnetic resonance imaging (MRI) data, positron emission tomography (PET) data or 3D rotational angiography (3DRA) data, and/or any information obtained from these or other imaging modalities. In some embodiments, the imaging apparatus 10 can track in-treatment patient, target, or ROI motion.

A reconstruction processor 40 can be operatively coupled to detector 24 and/or x-ray detector 34. In one embodiment, the reconstruction processor 40 is configured to generate patient images based on radiation received by detectors 24, 34 from the radiation sources 20, 30. It will be appreciated that the reconstruction processor 40 can be configured to be used to carry out the methods described more fully below. The apparatus 10 can also include a memory 44 suitable for storing information, including, but not limited to, processing and reconstruction algorithms and software, imaging parameters, image data from a prior or otherwise previously-acquired image (e.g., a planning image), treatment plans, and the like.

The x-ray imaging apparatus 10 can include an operator/user interface 48, where an operator of the x-ray imaging apparatus 10 can interact with or otherwise control the x-ray imaging apparatus 10 to provide input relating to scan or imaging parameters and the like. The operator interface 48 can include any suitable input devices, such as a keyboard, mouse, voice-activated controller, or the like. The x-ray imaging apparatus 10 can also include a display 52 or other human-readable element to provide output to the operator of the imaging apparatus 10. For example, the display 52 can allow the operator to observe reconstructed patient images and other information, such as imaging or scan parameters, related to operation of the x-ray imaging apparatus 10.

As shown in FIG. 2, the x-ray imaging apparatus 10 includes a controller (indicated generally as 60) operatively coupled to one or more components of the apparatus 10. The controller 60 controls the overall functioning and operation of apparatus 10, including providing power and timing signals to the x-ray source 30 and/or the therapeutic radiation source 20 and a gantry motor controller that controls rotational speed and position of the rotatable gantry 12. It will be appreciated that the controller 60 can encompass one or more of the following: a patient support controller, a gantry controller, a controller coupled to the therapeutic radiation source 20 and/or the x-ray source 30, a beamformer 36 controller, a controller coupled to the detector 24 and/or the detector 34, and the like. In one embodiment controller 60 is a system controller that can control other components, devices, and/or controllers.

In various embodiments, the reconstruction processor 40, the operator interface 48, the display 52, the controller 60 and/or other components may be combined into one or more components or devices.

The apparatus 10 may include various components, logic, and software. In one embodiment, the controller 60 comprises a processor, a memory, and software. By way of example and not limitation, an x-ray imaging apparatus and/or radiotherapy system can include various other devices and components (e.g., gantries, radiation sources, collimators, detectors, controllers, power sources, patient supports, among others) that can implement one or more routines or steps related to imaging and/or IGRT for a specific application, wherein a routine can include imaging, image-based pre-delivery steps, and/or treatment delivery, including respective device settings, configurations, and/or positions (e.g., paths/trajectories), which may be stored in memory. Furthermore, the controller(s) can directly or indirectly control one or more devices and/or components in accordance with one or more routines or processes stored in memory. An example of direct control is the setting of various radiation source or collimator parameters (power, speed, position, timing, modulation, etc.) associated with imaging or treatment. An example of indirect control is the communication of position, path, speed, etc. to a patient support controller or other peripheral device. The hierarchy of the various controllers that may be associated with an imaging apparatus can be arranged in any suitable manner to communicate the appropriate commands and/or information to the desired devices and components.

Moreover, those skilled in the art will appreciate that the systems and methods may be implemented with other computer system configurations. The illustrated aspects of the invention may be practiced in distributed computing environments where certain tasks are performed by local or remote processing devices that are linked through a communications network. For example, in one embodiment, the reconstruction processor 40 may be associated with a separate system. In a distributed computing environment, program modules may be located in both local and remote memory storage devices. For instance, a remote database, a local database, a cloud-computing platform, a cloud database, or a combination thereof can be utilized with x-ray imaging apparatus 10.

X-ray imaging apparatus 10 can utilize an exemplary environment for implementing various aspects of the invention including a computer, wherein the computer includes the controller 60 (e.g., including a processor and a memory, which may be memory 44) and a system bus. The system bus can couple system components including, but not limited to, the memory to the processor, and can communicate with other systems, controllers, components, devices, and processors. Memory can include read only memory (ROM), random access memory (RAM), hard drives, flash drives, and any other form of computer readable media. Memory can store various software and data, including routines and parameters, which may comprise, for example, a treatment plan.

The therapeutic radiation source 20 and/or x-ray source 30 can be operatively coupled to a controller 60 configured to control the relative operation of the therapeutic radiation source 20 and the x-ray source 30. For example, the x-ray source 30 can be controlled and operated simultaneously with the therapeutic radiation source 20. In addition, or alternatively, the x-ray source 30 can be controlled and operated sequentially with the therapeutic radiation source 20, depending on the particular treatment and/or imaging plan being implemented.

It will be appreciated that the x-ray source 30 and the x-ray detector 34 can be configured to provide rotation around the patient during an imaging scan in a number of ways. In one embodiment, synchronizing the motion and exposure of the x-ray source 30 with the longitudinal motion of the patient support 18 can provide a continuous helical acquisition of a patient image during a procedure. In addition to continuous rotation of the radiation sources 20, 30 and detector(s) 24, 34 (e.g., continuous and constant rotation of the gantry with constant patient motion speed), it will be appreciated that other variations can be employed without departing from the scope of the disclosed technology. For example, the rotatable gantry 12 and patient support can be controlled such that the gantry 12 rotates in a "back-and-forth" manner (e.g., alternating clockwise rotation and counterclockwise rotation) around a patient supported on the patient support (as opposed to continuously, as is described above) as the support is controlled to move (at a constant or variable speed) relative to the rotatable gantry 12. In another embodiment, with successive step-and-shoot circular scans, movement of the patient support 18 in the longitudinal direction (step) alternates with a scanning revolution by the rotatable gantry 12 (shoot) until the desired volume is captured. The x-ray imaging apparatus 10 is capable of volume-based and planar-based imaging acquisitions. For example, in various embodiments, the x-ray imaging apparatus 10 may be used to acquire volume images and/or planar images (e.g., via use of the x-ray source 30 and the detector 34) and execute the associated processing, including scatter estimation/correction methods described below.

Various other types of radiation source and/or patient support movement may be utilized to achieve relative motion of the radiation source and the patient for generation of projection data. Non-continuous motion of the radiation source and/or patient support, continuous but variable/non-constant (including linear and non-linear) movement, speed, and/or trajectories, etc., and combinations thereof may be used, including in combination with the various embodiments of radiotherapy devices 10 described above.

In one embodiment, the gantry 12 rotation speed, the patient support 18 speed, the beamformer 36 shape, and/or the detector 34 readout could all be constant during image acquisition. In other embodiments, one or more of these variables could change dynamically during image acquisition. The gantry 12 rotation speed, patient support 18 speed, beamformer 36 shape, and/or detector 34 readout can be varied to balance different factors, including, for example, image quality and image acquisition time.

In other embodiments, these features can be combined with one or more other image-based activities or procedures, including, for example, patient set up, adaptive therapy monitoring, treatment planning, etc.

There are many determinants of image quality (e.g., X-ray source focal spot size, detector dynamic range, etc.). A limitation of kV CBCT image quality is scatter. Various approaches can be used to reduce scatter. One approach is to use an anti-scatter grid (which collimates the scatter). However, it can be problematic to implement a scatter grid on a kV imaging system, including for motion tracking and correction. Accurately estimating scatter in the projection data is necessary to improve the quality of the image data. In various embodiments, scatter in the projection data acquired in a wide aFOV region of the detector 34 can be estimated based on the (relatively scatter-free) projection data acquired in a narrow aFOV region within the wide aFOV region.

In particular, data can be acquired in a narrow region of a target using a narrow aperture, such that the scatter is either minimal/negligible or can be accurately obtained using simple techniques. For example, the narrow aperture data can be scatter-free, nearly scatter-free, or is itself scatter-corrected, using kernel-based scatter correction, collimator shadow fitting estimation, etc. Narrow apertures can be of any size suitable for a particular application, including, for example in some embodiments, 2-3 mm, 1 cm, 2 cm, and/or any size smaller than the wide aperture, etc. Data can also be acquired in a wide region of the target using a wide aperture, where the narrow region is within the wide region. Wide apertures can also be of any size suitable for a particular application, including, for example in some embodiments, 5 cm, 10 cm, 15 cm, 20 cm, and/or any size larger than the narrow aperture, etc. In various embodiments, the narrow aperture data can be used to improve the kernel-based scatter estimations and correction of the CBCT data acquired in the wide region. The process of improving the scatter estimation using the narrow scan within the wide scan can be accomplished in either the projection domain or in the reconstruction, as discussed in detail below. The process can also be conducted in either non-iterative or iterative manners.

Figure 3:
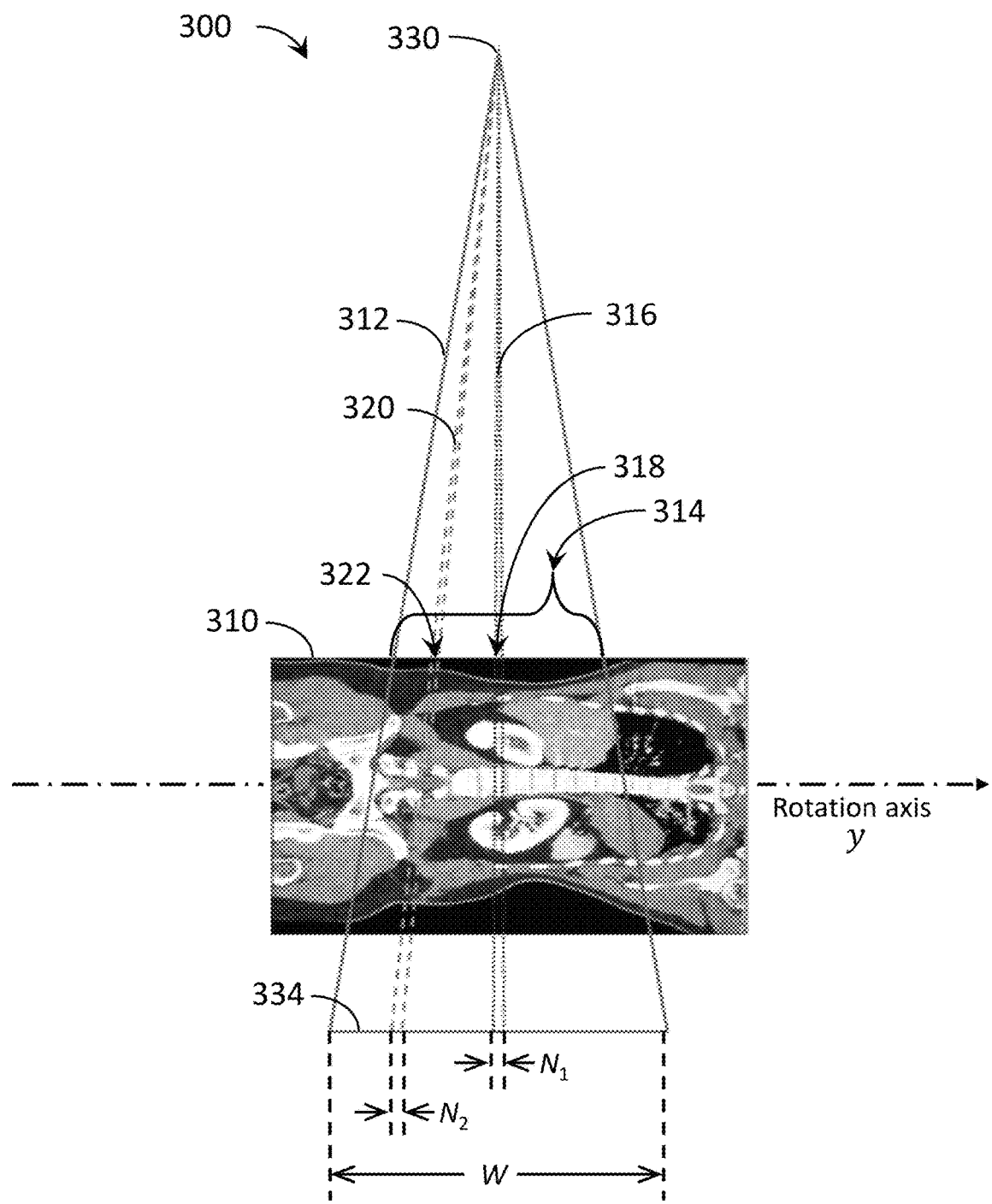
FIG. 3 is a diagrammatic illustration of an exemplary scan design for imaging an axial region of a target.

In an exemplary embodiment, FIG. 3 shows an illustration of an exemplary scan design 300 for imaging an axial region of a target 310. A large/wide aFOV beam 312 is used to scan a wide region 314 of the target 310, shown with an axial length W. A small/narrow aFOV beam 316 is used to scan a narrow region 318, shown with an axial length $N_1$. The narrow region 318 is within the wide region 314 and axial length $N_1$ is less than axial length W. In some embodiments, a plurality of narrow scans may be utilized to improve accuracy (scatter estimation), especially if portions of the wide region 314 exhibit axial variance. For example, in one embodiment, another narrow aFOV beam 320 can be used to scan another narrow region 322, shown with an axial length $N_2$. The narrow region 322 is also within the wide region 314 and axial length $N_2$ is less than axial length W. All of the exemplary beams 312, 316, 320 are shown projecting from (collimated) source 330, through the target 310, and incident on detector 334. Any number of narrow scans may be used within the wide region 314.

The axial length $N_1$ is small enough such that the narrow scan projection data for the narrow region 318 is scatter-free, has scatter that is minimal, and/or has scatter that can be easily obtained/corrected. A portion of the wide scan projection data for the wide region 314 (which does contain scatter since it is from a wide scan) overlaps the narrow region 318. Comparing (e.g., finding the difference between) the projection data from the wide scan in the narrow region 318 (with scatter) and the projection data from the narrow scan in the narrow region 318 (without scatter) results in an accurate estimate (essentially a measurement) of true scatter in the narrow region 318. The comparison can be done in either the projection domain or in the reconstruction, as discussed in detail below. In this embodiment, the wide scan is a circular scan, but other embodiments can make use of helical and/or other scan trajectories.

After this comparison, the true scatter for the narrow region 318 can be used to optimize a scatter estimation technique applied to the entire wide region 314 with high confidence. This can be especially effective if the target is minimally variant in the wide region 314. The optimization can be conducted in either non-iterative or iterative manners, as discussed in detail below. In some embodiments, multiple narrow aperture data sets (e.g., from narrow regions 318, 322) can be acquired in the axial range of a wide aFOV CBCT scan (e.g., from wide region 314) to improve the scatter correction.

In one embodiment, the scatter estimation technique utilizes kernel-based scatter estimation/correction. For example, a kernel-based scatter estimation technique applied to the projection data from the wide scan in the narrow region 318 can be constrained so that the scatter estimate generated by the kernel-based scatter estimation technique yields the determined accurate scatter estimate for the narrow region 318, since the true scatter is known for the narrow region 318. Then, the constrained (optimized) kernel-based scatter estimation technique can be applied to the remainder of the wide region 314 with improved results (e.g., versus an unconstrained application). Kernel-based techniques may be based on patient-dependent and/or system-dependent factors to improve accuracy.

In some embodiments, more than one wide aFOV region (e.g., 314) may be scanned as part of a larger axial range. Each of these wide aFOV regions 314 can include one or more narrow aFOV regions (e.g., 318, 322).

As shown in FIG. 3, one embodiment of a scan design 300 can include a large aFOV CBCT scan of a patient's chest (314) and a complementary scan of a region with a narrow aperture (318). In some embodiments, for more optimal performance, multiple narrow aperture scans (318, 322) can be determined and acquired where the positions are distributed inside the large aFOV (314). The narrow aperture scan(s) associated with regions 318, 322 can use clinically valid protocols, from which accurate reconstruction of the range covered by the narrow aperture 316, 320 can also be used for clinical applications. In some embodiments, the narrow aperture scan, when only used for improving scatter correction, can use fast gantry rotation and sparse angular sampling to minimize the impact on total scan time and patient dose.

When the aperture created by the beamformer 36 is sufficiently narrow (e.g., beams 316, 320 associated with narrow regions 318, 322, respectively), the scatter in the projection data is essentially negligible. Hence, in one embodiment, the narrow aperture data can be used as scatter-free data. In another embodiment, some simple techniques can be effective and accurate to estimate the small amount of scatter in the projection data. In this manner, the narrow aperture data is scatter corrected to become scatter-free data. For example, as mentioned above, simple and effective scatter correction approaches to the narrow aperture data can include a fitting using the data in the shadows of the beamformer collimators that form the apertures, kernel-based scatter correction, etc. References to the narrow aperture data as scatter-free data may be the result of an initial scatter correction to the narrow aperture data.

The following flow charts and block diagrams illustrate exemplary configurations and methodologies associated with scatter estimation and correction in accordance with the systems described above. The exemplary methodologies may be carried out in logic, software, hardware, or combinations thereof. In addition, although the procedures and methods are presented in an order, the blocks may be performed in different orders, including series and/or parallel. Further, additional steps or fewer steps may be used.

Figure 4:
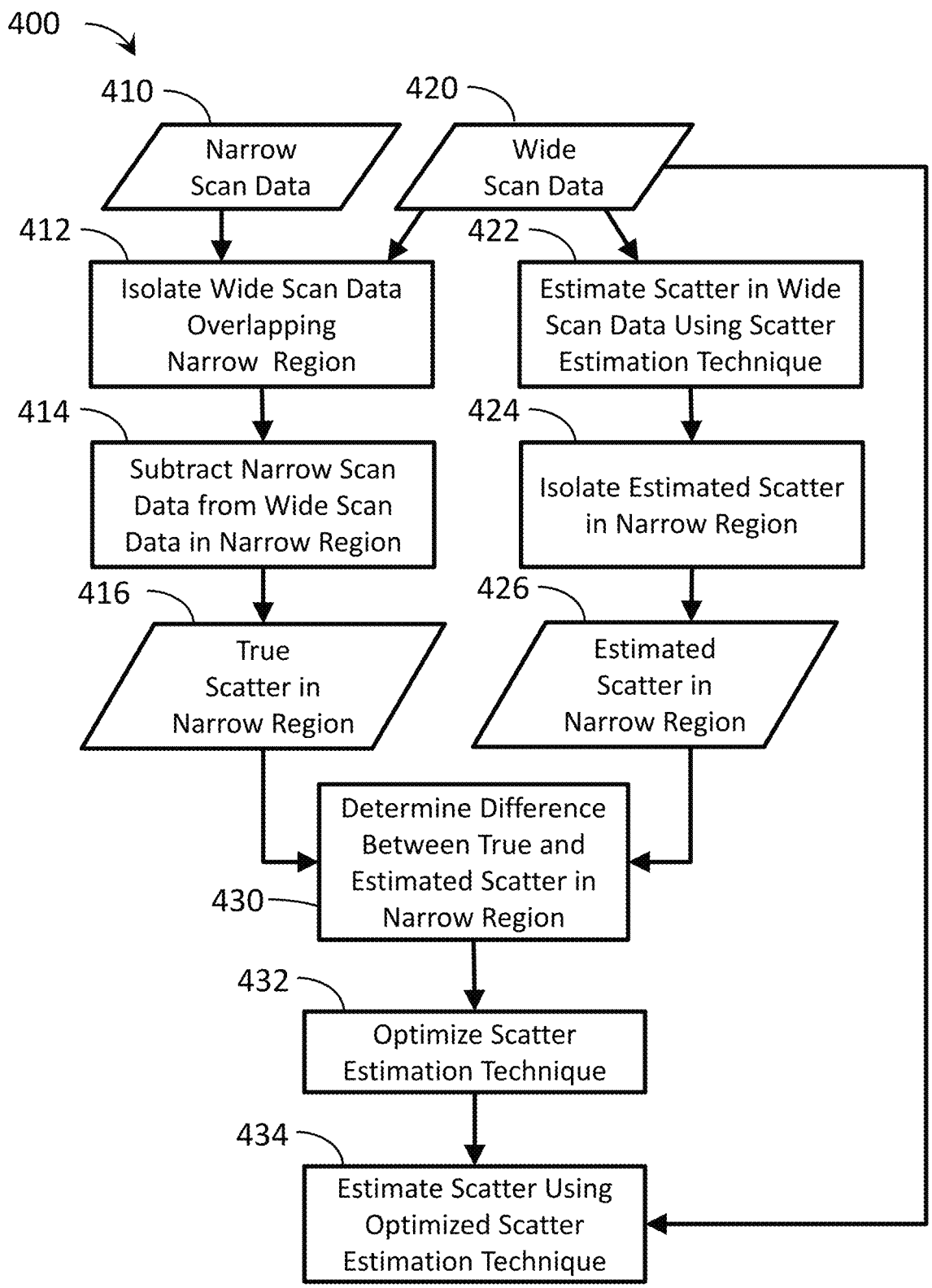
FIG. 4 is a flow chart depicting an exemplary method of scatter estimation in the projection data domain using a scan design with a narrow scan region within a wide scan region.

FIG. 4 is a flow chart depicting an exemplary method 400 of scatter estimation in the projection data domain using a scan design with a narrow scan region within a wide scan region, such as those described above. Narrow scan data 410 from a narrow region and wide scan data 420 from a wide region are provided or received, for example, from a data acquisition using the imaging apparatus 10 described above. The narrow region is within the wide region, as described above, for example, in FIG. 3. The narrow scan data 410 is scatter-free, while the wide scan data 420 contains scatter. In this embodiment, step 412 isolates the portion of the wide scan data 420 that overlaps the narrow region. Next, at step 414, the method 400 subtracts the narrow scan data 410 (without scatter) from the isolated portion of the wide scan data 420 (with scatter) that corresponds to the narrow region. The resulting data is the true (measured) scatter 416 in the narrow region.

At step 422, the method 400 estimates the scatter in the wide scan data 420 using a scatter estimation technique, which may include, for example, a kernel-based scatter estimation technique. Next, at step 424, the estimated scatter in the narrow region is isolated from the estimated scatter for the wide region. The resulting data is the estimated scatter 426 in the narrow region, using the scatter estimation technique.

Then, at step 430, the method 400 determines the difference between the true (measured) scatter 416 and the estimated scatter 426 in the narrow region. This difference can be used to optimize the scatter estimation technique at step 432. For example, the scatter estimation technique can be optimized by minimizing the difference between the estimated scatter 426 and the true scatter 416. Minimizing the difference can include various types of fitting processes. In one non-iterative embodiment, the optimization process can include a least-square solution. Then, at step 434, the optimized (e.g., fitted kernel-based) scatter estimation technique can be used to re-estimate the scatter in the rest of the wide scan data 420 with improved accuracy. The scatter estimate can be used during reconstruction of the wide region.

Figure 5:
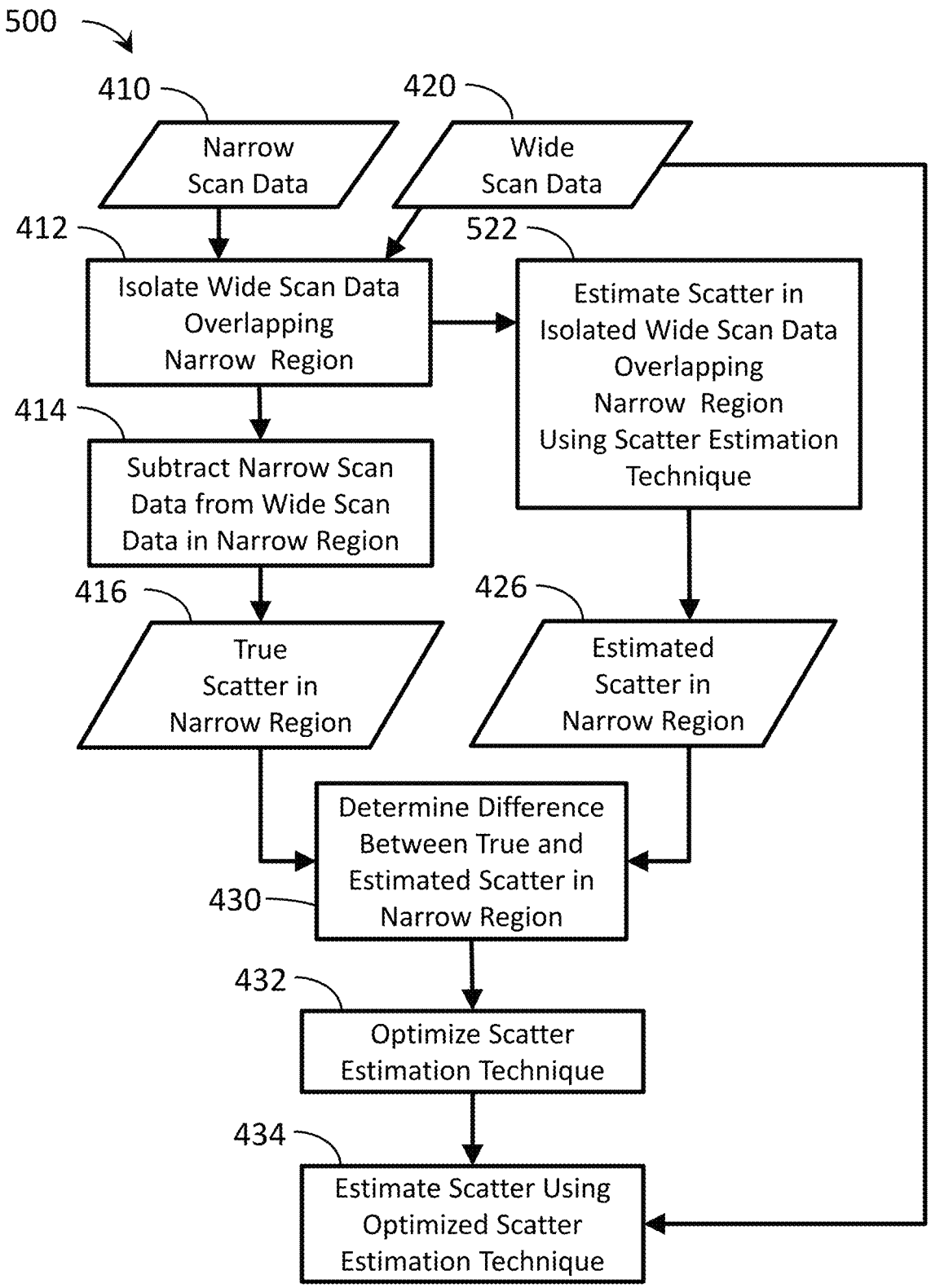
FIG. 5 is a flow chart depicting another exemplary method of scatter estimation in the projection data domain using a scan design with a narrow scan region within a wide scan region.

FIG. 5 is a flow chart depicting another exemplary method 500 of scatter estimation in the projection data domain using a scan design with a narrow scan region within a wide scan region, such as those described above. Method 500 is similar to method 400, except that in this embodiment, at step 522, the method 500 only initially estimates the scatter in the isolated portion of the wide scan data 420 overlapping the narrow region using a scatter estimation technique. This is computationally less intensive than estimating the scatter in the entire wide scan data 420 before isolating the narrow region, as in steps 422 and 424 of method 400. In this embodiment, the isolated wide scan data can come directly from step 412. The resulting data is the estimated scatter 426 in the narrow region, using the scatter estimation technique. The other steps are performed as in method 400.

Figure 6:
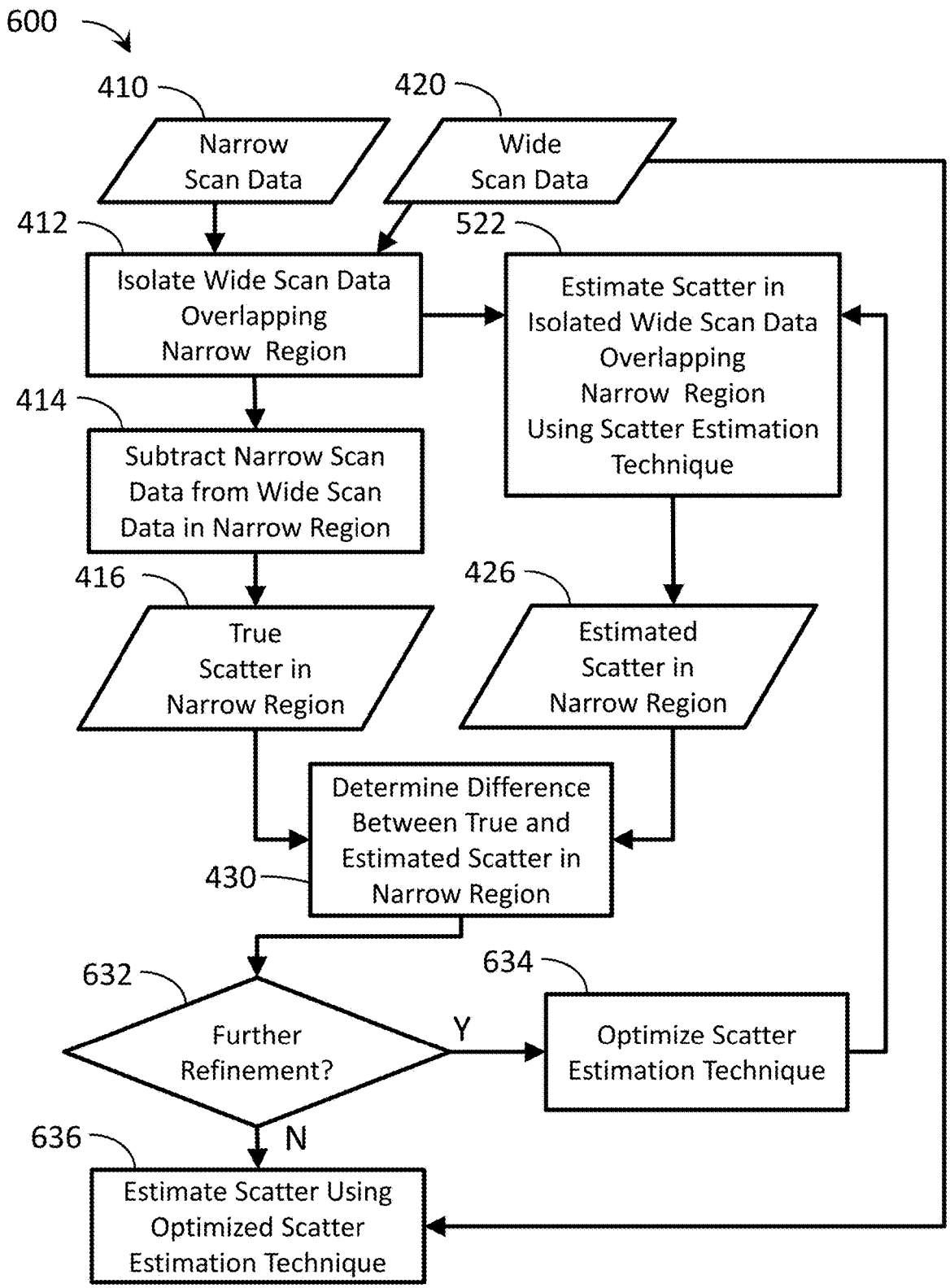
FIG. 6 is a flow chart depicting an exemplary iterative method of scatter estimation in the projection data domain using a scan design with a narrow scan region within a wide scan region.

FIG. 6 is a flow chart depicting an exemplary iterative method 600 of scatter estimation in the projection data domain using a scan design with a narrow scan region within a wide scan region, such as those described above. Method 600 is similar to method 500, except that in this embodiment, after step 430, method 600 implements an iterative optimization of the scatter estimation technique. In particular, at step 632, the method 600 determines if the difference between the true (measured) scatter 416 and the estimated scatter 426 in the narrow region needs further refinement or optimization. In various embodiments, to determine if further refinement is needed at step 632, the difference from step 430 (which represents how close the estimated scatter 426 from the scatter estimation technique is to the true scatter 416) may be subjected to a variety of conditions/analysis, including, for example, the difference may be compared to a threshold value, the difference between the current iteration and prior iteration(s) may be compared to a threshold value or rate (e.g., to determine the convergence rate of the iterative/incremental improvements to the estimate), the number of iterations (loops back to step 522) may be compared to a threshold value, the time associated with the scan and/or iteration process may be compared to a threshold value (e.g., for considering overall workflow), combinations of these and/or other factors, including weighted averages, etc.

If the analysis at step 632 determines that the difference from step 430 needs further refinement, the method 600 proceeds to step 634 to optimize the scatter estimation technique in view of the difference from step 430. For example, the scatter estimation technique can be optimized by minimizing the difference between the estimated scatter 426 and the true scatter 416. Minimizing the difference can include various types of fitting processes. In case of multiple iterations, step 634 may be a further optimization.

If the analysis at step 632 determines that the difference from step 430 does not need further refinement, the method 600 proceeds to step 636 to apply the optimized (e.g., fitted kernel-based) scatter estimation technique to the rest of the wide scan data 420 with improved accuracy.

In this manner, acquired narrow aperture scan data, including in conjunction with kernel-based scatter estimation, can be used to improve the scatter estimation of wide aperture scan data in imaging modalities. For example, the imaging can include x-ray imaging, CT imaging, CBCT imaging, etc. Kernel-based scatter estimation and correction, including refined/optimized embodiments, can be employed to improve the image quality and quantitation. A beamformer (e.g., with a set of collimators) can effectively block part of the beams to form an aperture for imaging, where the aperture size can be varied to allow very narrow aperture data acquisitions. The aperture position relative to the patient can be varied relative to the patient. In various embodiments, a kernel-based scatter estimation of the data from the large aFOV (wide region) scan is compared to the measured scatter in the small aFOV (narrow region) at the same angles. The measured scatter is the result of subtracting the scatter-free data of the narrow aperture scan from the data including scatter at the same region at the same angles/views.

The kernel-based scatter estimation can be optimized by minimizing the difference between the estimated scatter and the measured scatter. The optimized kernel-based scatter estimation can then be applied to the rest of the large aFOV data to improve the accuracy of scatter correction.

As mentioned above, optimizing the scatter estimation technique can also occur in the reconstruction domain, where the image reconstructed from the narrow aperture scan data can be deemed a scatter-free image. The reconstruction of the same region from the wide aperture scan data, for example, with a kernel-based scatter correction technique, can be compared with the scatter-free image. The scatter correction technique can be optimized to minimize the difference. In some embodiments, for example, for intended clinical applications, the difference can be focused on only some image aspects. For example, if the wide aFOV image is used for radiation therapy adaptive planning, the quantitative accuracy is critical for dose calculation and low-contrast recovery is critical for tumor detection and delineation for dose planning.

Figure 7:
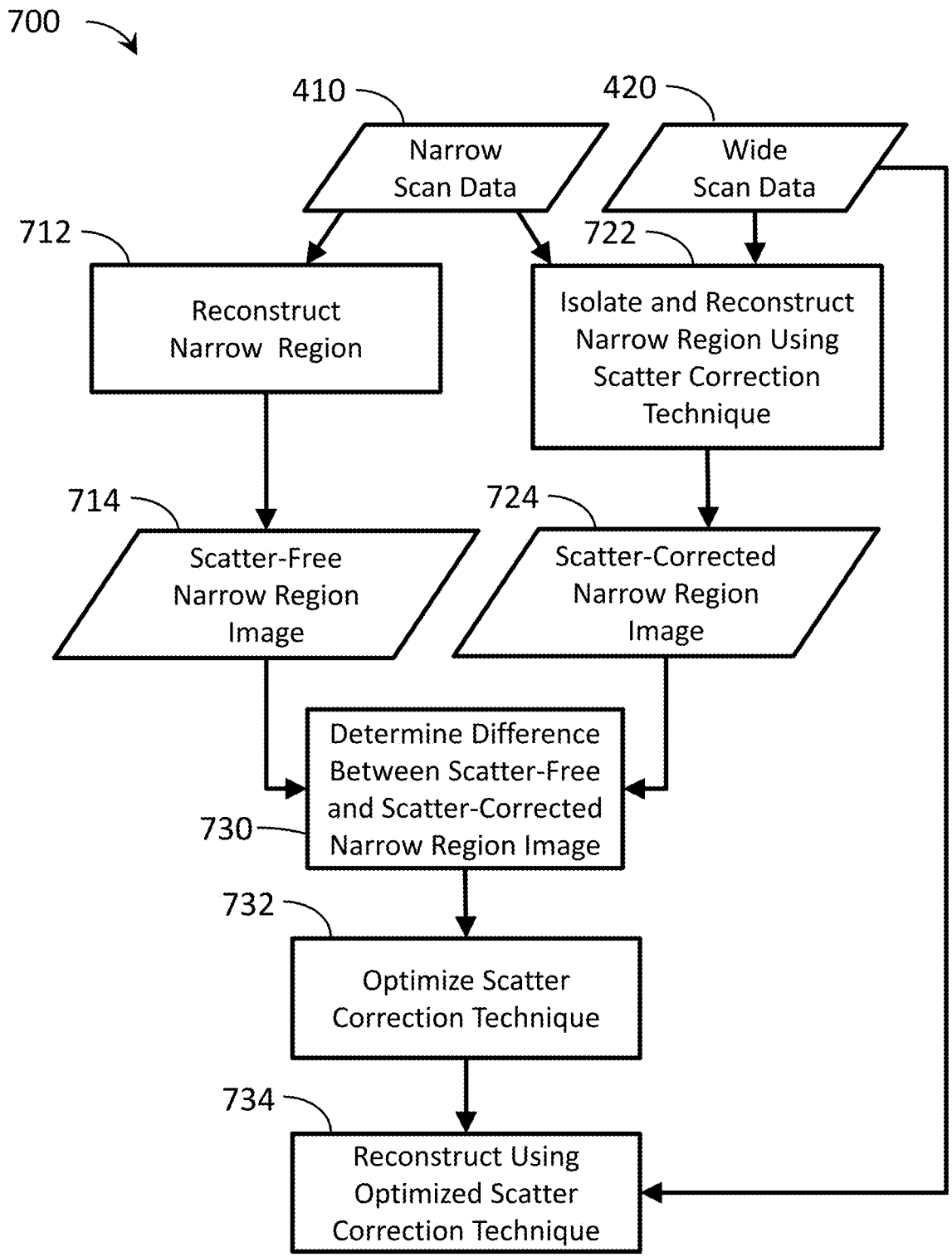
FIG. 7 is a flow chart depicting an exemplary method of scatter correction in the reconstruction domain using a scan design with a narrow scan region within a wide scan region.

FIG. 7 is a flow chart depicting an exemplary method 700 of scatter correction in the reconstruction domain using a scan design with a narrow scan region within a wide scan region, such as those described above. Narrow scan data 410 from a narrow region and wide scan data 420 from a wide region are provided or received, for example, from a data acquisition using the imaging apparatus 10 described above. The narrow region is within the wide region, as described above, for example, in FIG. 3. The narrow scan data 410 is scatter-free, while the wide scan data 420 contains scatter. In this embodiment, step 712 reconstructs the narrow region using the narrow scan data 410. The resulting image is a scatter-free narrow region image 714.

At step 722, the method 700 isolates and reconstructs the narrow region using the wide scan data 420 using a scatter correction technique, which may include, for example, a kernel-based scatter estimation/correction technique. The resulting image is a scatter-corrected narrow region image 724.

Then, at step 730, the method 700 determines the difference between the scatter-free narrow region image 714 and the scatter-corrected narrow region image 724. This difference can be used to optimize the scatter correction technique at step 732. For example, the scatter correction technique can be optimized by minimizing the difference between the scatter-free narrow region image 714 and the scatter-corrected narrow region image 724. Minimizing the difference can include various types of fitting processes. In one non-iterative embodiment, the optimization process can include a least-square solution. Then, at step 734, the optimized (e.g., fitted kernel-based) scatter correction technique can be used to reconstruct the wide region using the wide scan data 420 with improved accuracy.

Figure 8:
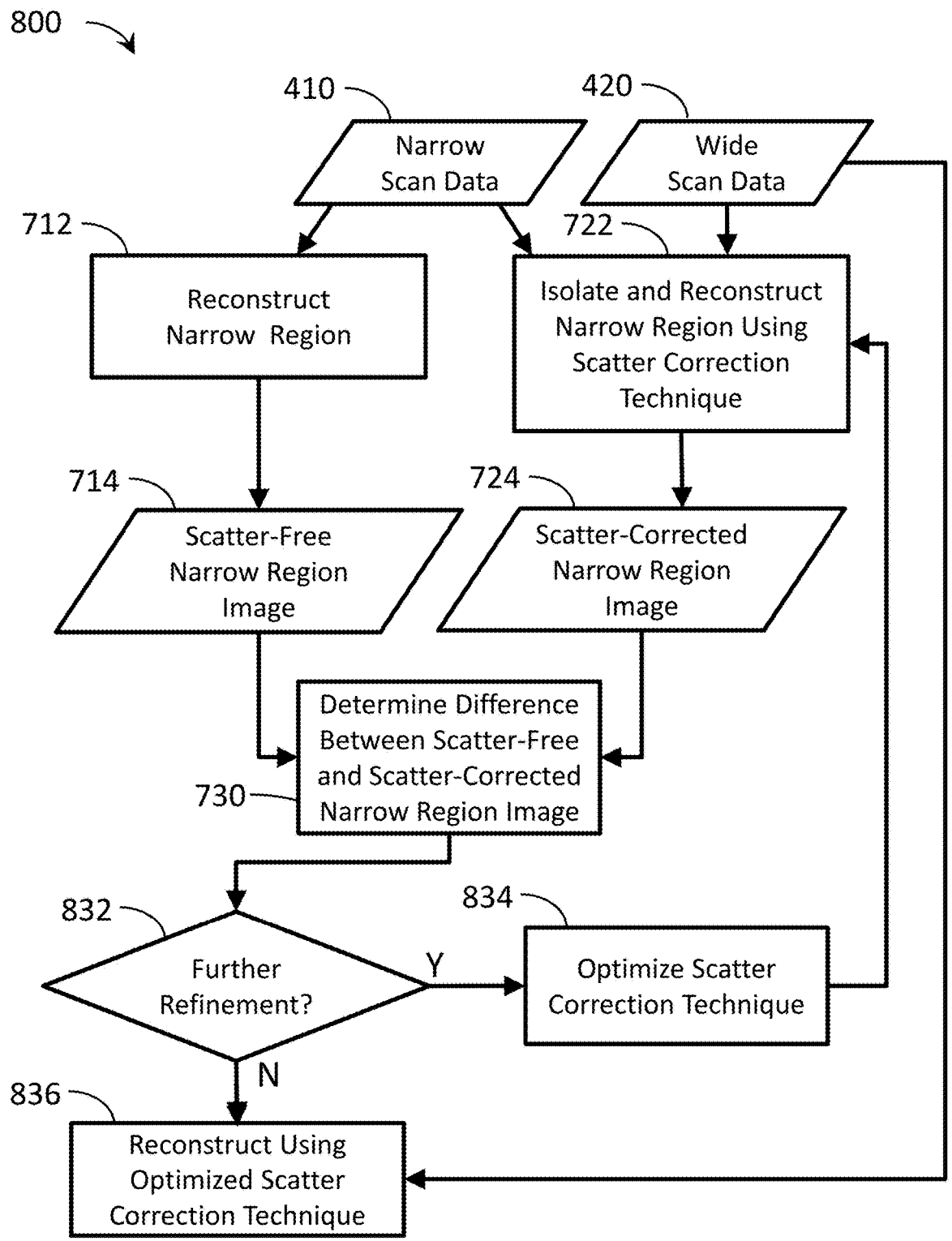
FIG. 8 is a flow chart depicting an exemplary iterative method of scatter correction in the reconstruction domain using a scan design with a narrow scan region within a wide scan region.

FIG. 8 is a flow chart depicting an exemplary iterative method 800 of scatter correction in the reconstruction domain using a scan design with a narrow scan region within a wide scan region, such as those described above. Method 800 is similar to method 700, except that in this embodiment, after step 730, method 800 implements an iterative optimization of the scatter correction technique. In particular, at step 832, the method 800 determines if the difference between the scatter-free narrow region image 714 and the scatter-corrected narrow region image 724 needs further refinement or optimization. In various embodiments, to determine if further refinement is needed at step 832, the difference from step 730 (which represents how close the scatter-corrected narrow region image 724 using the scatter correction technique is to the scatter-free narrow region image 714) may be subjected to a variety of conditions/analysis, including, for example, the difference may be compared to a threshold value, the difference between the current iteration and prior iteration(s) may be compared to a threshold value or rate (e.g., to determine the convergence rate of the incremental improvements to the corrected image), the number of iterations (loops back to step 722) may be compared to a threshold value, the time associated with the scan and/or iteration process may be compared to a threshold value (e.g., for considering overall workflow), combinations of these and/or other factors, including weighted averages, etc.

If the analysis at step 832 determines that the difference from step 730 needs further refinement, the method 800 proceeds to step 834 to optimize the scatter correction technique in view of the difference from step 730. For example, the scatter correction technique can be optimized by minimizing the difference between the scatter-corrected narrow region image 724 and the scatter-free narrow region image 714. Minimizing the difference can include various types of fitting processes. In case of multiple iterations, step 834 may be a further optimization.

If the analysis at step 832 determines that the difference from step 730 does not need further refinement, the method 800 proceeds to step 836 to reconstruct the wide region by applying the optimized (e.g., fitted kernel-based) scatter correction technique to the rest of the wide scan data 420 with improved accuracy.

As mentioned above, the narrow aperture data can be acquired using a clinically valid protocol. In these embodiments, the data can be used to reconstruct images of this portion of the patient accurately. The image reconstructed from the large aFOV data of the same portion of the patient can be compared to the image from the narrow aperture reconstruction. The kernel-based scatter correction of the large aFOV data (wide region) can be optimized so that the reconstructed image matches the narrow aperture image at the same portion (narrow region). Consequently, the reconstructed image of the rest of the wide region is improved with the optimized kernel-based scatter correction. In one embodiment, the kernel-based scatter correction can be optimized by matching the large aFOV (wide region) image and the narrow aperture image at the same portion of the patient (narrow region) using clinically desired criteria. For example, one criterium is to match low contrast recovery for tumor detection and delineation. Another criterium is to match the quantitative accuracy for dose simulation and dose planning for adaptive radiation therapy.

Various factors may be considered to determine whether to execute the above methods in the projection data domain and/or the reconstruction domain, including, for example, based on accuracy, time, workflow, available data, etc. In some situations, only one domain may be possible or one domain may be preferable. For example, with reference to FIG. 3, where the narrow region beam 320 is oblique, as shown, the narrow aperture data does not allow for the reconstruction of an accurate image. Therefore, narrow scan data associated with the narrow region 322 may only be used to improve the scatter estimation in the projection domain.

In various embodiments, the reconstruction of images can be analytical reconstruction and/or iterative reconstruction.

The details of the narrow scan(s) (including, the number, axial location, angle, size, narrow/wide size ratio, etc.) for the narrow region(s) (e.g., 318, 322, as shown in FIG. 3) can be determined and/or optimized through various techniques. In embodiments where the wide scan(s) are not yet complete, determining the details of the narrow scan(s) can include determining details of the wide scan(s) as well, including, for example, number, size, ratio, etc. Optimization processes can be executed to determine the narrow and/or wide scan details (including, the number, axial location, angle, size, narrow/wide size ratio, etc.) to optimize the various factors discussed above, including total scan time, workflow, etc. For example, in some embodiments, the narrow scans can be determined from prior images (e.g., planning CT images, CBCT images from prior sub-session of treatment, etc.). In some embodiments, narrow scans can be selected from a bank of pre-determined narrow scans suitable for particular wide regions, including based on typical uniformity/variance and narrow areas suitable as the basis for the wider region. In other embodiments, for example, when prior images are not available, the narrow scans can be determined on-the-fly by using an image reconstructed from a scout scan and/or a wide region scan.

For example, in one embodiment, a relatively quick reconstruction of wide scan data can be started after the wide region scan acquires sufficient data for acceptable image reconstruction. The reconstructed image of the wide region can then be used to identify one or more narrow scans, for example, based on the uniformity (or lack thereof), axial length, use of a clinical protocol or a protocol only for scatter correction, which can include fewer projection angles, larger pitch for helical scan, etc. of the wide region. In some embodiments, other factors, such as workflow, may be considered in determining the number of narrow scans. In one embodiment, a computer algorithm/analysis can automatically determine the details of the narrow scan(s) based on the reconstructed image of the wide region. In another embodiment, a user can determine the details of the narrow scan(s) based on a review of the reconstructed image of the wide region. The narrow region information can then be fed back to the system to control the narrow scans.

Figure 9:
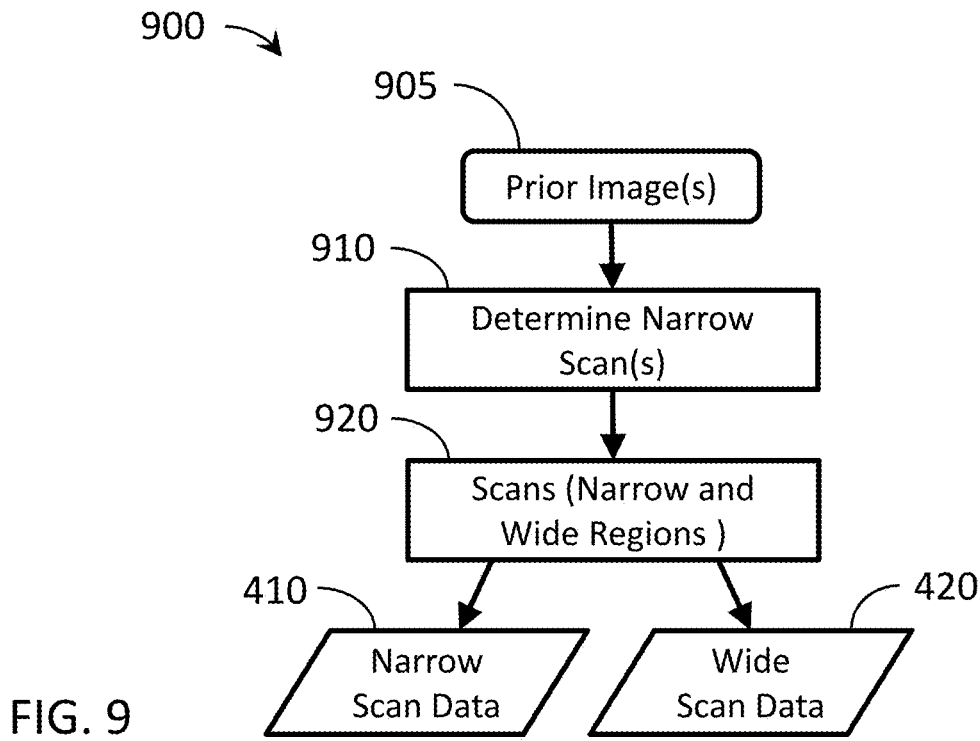
FIG. 9 is a flow chart depicting an exemplary method of determining a narrow scan from prior image data for use in a narrow/wide scan design.

For example, FIG. 9 is a flow chart depicting an exemplary method 900 of determining a narrow scan from prior image data for use in a narrow/wide scan design, such as those described above. Prior image data 905 of the patient (e.g., a prior image, which may be a previously-acquired planning image, including a prior CT image) are provided or received, for example, from another source or a data acquisition using the x-ray imaging apparatus 10 described above. At step 910, the method 900 determines the narrow scan details based on the prior image data 905, as discussed above. As mentioned above, in this embodiment, determining the details of the narrow scan(s) can include determining wide scan(s) details, including the optimization processes. Then, at step 920, the method 900 initiates the narrow and wide region scans, for example, using the imaging apparatus 10 described above. The resulting data is the narrow scan data 410 for the narrow region(s) and the wide scan data 420 for the wide region. Scan data 410, 420 may be used in accordance with scatter estimation and correction methods described above.

Figure 10:
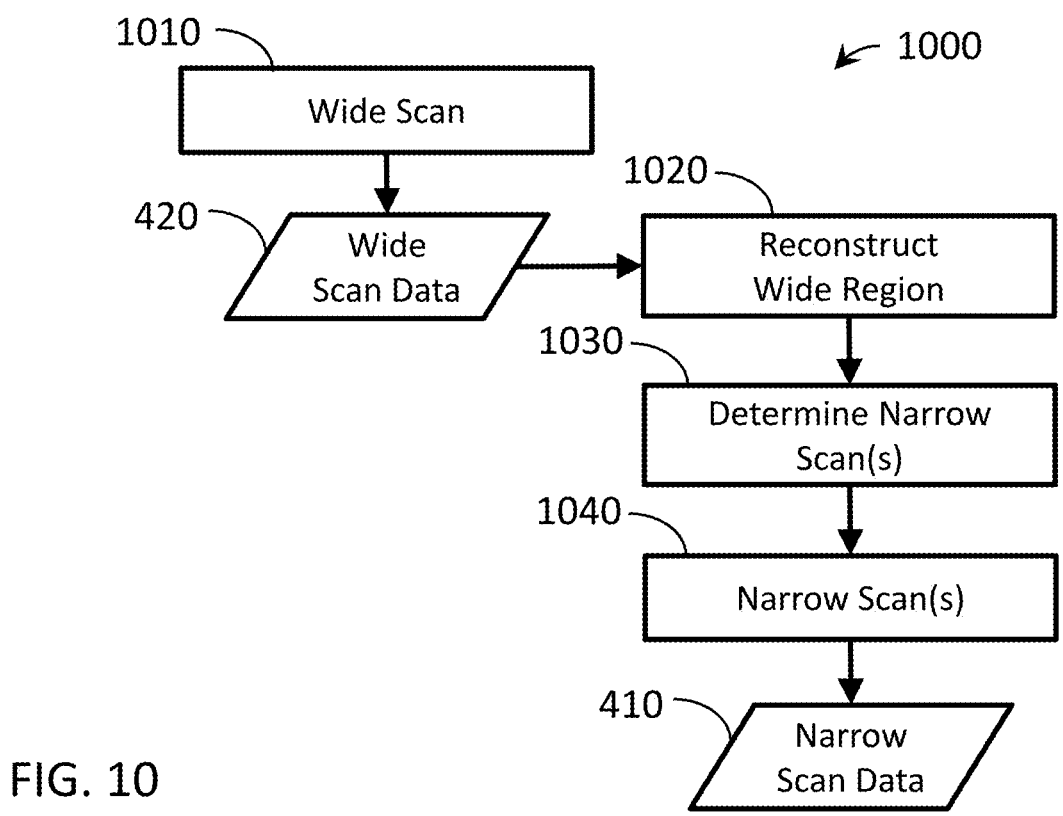
FIG. 10 is a flow chart depicting an exemplary method of determining a narrow scan from wide scan data for use in a narrow/wide scan design.

In another embodiment, FIG. 10 is a flow chart depicting an exemplary method 1000 of determining a narrow scan from wide scan data for use in a narrow/wide scan design, such as those described above. At step 1010, the method 1000 executes a wide region scan of the patient to support imaging and/or therapeutic objectives, for example, using the imaging apparatus 10 described above. The resulting data is the wide scan data 420 for the wide region. Then, at step 1020, the method 1000 starts to reconstruct the wide scan data 420. At step 1030, based on at least a partially reconstructed image of the patient, the method 1000 determines the narrow scan details based on the reconstructed image, as discussed above. Then, at step 1040, the method 1000 initiates the narrow scan(s), for example, using the imaging apparatus 10 described above. The resulting data is the narrow scan data 410 for the narrow region(s). Scan data 410, 420 may be used in accordance with scatter estimation and correction methods described above.

In this manner, the narrow aperture scan (including, e.g., number, location, angle, size, etc.) can be determined using prior images or determined on-the-fly with the availability of data/image information from the wide aperture scan. For example, when the narrow aperture scan size and position, as well as the angle at which narrow aperture data is acquired, are determined on-the-fly, an image of the patient is first obtained from the wide region scan. Then, a portion or the entirety of the wide scan data is used to obtain the image of the patient, including image reconstruction while the large aFOV data acquisition (wide region scan) is still going on (concurrent reconstruction/acquisition) or reconstruction after the large aFOV scan is finished. The determination of the narrow aperture scan details can use algorithms/software that use the image non-uniformity determined from the obtained image of the patient.

When the above apparatus and methods are used for scatter correction in the projection domain, it can be applied on each projection view, where each projection view is a planar image. In one embodiment, using planar x-ray image(s) (e.g., for motion tracking), a previously available volume image may be used with a kernel-based scatter estimation technique to estimate the scatter in the planar image for scatter correction (e.g., for contrast improvement). The above methods can utilize the measured scatter in the narrow aperture data to improve the kernel-based scatter estimation.

In another embodiment, first a planar image can be acquired with a wide aperture and collimator shadow regions. Next, the collimator shadow can be used to estimate the scatter in the planar image, using a shadow fitting technique. Then, the narrow aperture data can be used to measure scatter in the narrow region. The result can be used to refine the shadow fitting technique for the wide aperture scatter estimation.

The above apparatus and methods offer several advantages over existing techniques. For example, the apparatus and methods can improve the performance of conventional kernel-based scatter estimation and correction approaches in CBCT. In particular, the improvements can be manifest in the context of patient scans of highly non-uniform regions and with large axial field-of-view.

In one embodiment, using a kernel-based model for scatter estimation/correction, when optimized for the region covered by the narrow aperture, is more accurate for the rest of the wide region than the conventional kernel-based approach. The narrow aperture data (scatter-free) provides the complementary information to optimize or constrain the kernel-based model, resulting in improved accuracy of the kernel-based model during scatter estimation/correction. In this manner, the optimization process can be very straightforward but very effective.

As mentioned above, the narrow region scan can use a clinically valid protocol that allows accurate reconstruction of the narrow region covered by the aperture. Therefore, the dose and scan time associated with the narrow scan is fully utilized and not wasted. In other embodiments, the narrow region scan can be for scatter correction purposes only. In these embodiments, the acquisition can use fast gantry rotation and/or acquire angularly sparse data. Consequently, the impact of the narrow region scan on patient dose and scan time can be minimized.

Various embodiments can utilize different scan geometries, detector positioning (including offset detectors), and/or beamformer window shapes. In some embodiments, the narrow and/or wide scan trajectories can be 180 degrees if the detector is centered and up to 360 degrees if the detector is offset.

As is discussed above, aspects of the disclosed technology can be utilized in a radiotherapy device and method that make use of integrated kilovoltage (kV) CT for use in conjunction with or as part of IGRT. In accordance with one embodiment, the image acquisition methodology includes or otherwise makes use of a helical source trajectory (e.g., a continuous source rotation about a central axis together with longitudinal movement of a patient support through a gantry bore) or a circular scan with a kV beam collimation, together with fast slip ring rotation, to provide kV CT imaging on a radiation therapy delivery platform. It will be appreciated that such an implementation can provide reduced scatter and improved scatter estimation to enable kV images of higher quality than conventional systems.

It will be further appreciated that any potential increased scan time associated with multiple beam rotations to complete a volume image can be mitigated or otherwise offset by high kV frame rates, high gantry rates, and/or sparse data reconstruction techniques. It will be further appreciated that the above-described provision of a selectively controllable collimator/beamformer allows for a system where a user can trade off or otherwise vary image acquisition time versus image quality, depending on the specific application and/or clinical need. It also will be appreciated that the radiotherapy delivery device can be controlled to provide half- or single-rotation cone beam CT scans (with potential reduced image quality due to scatter) with fast image acquisition time (e.g., for motion tracking), as well as circular or continuous helical acquisition with a narrow/slit fan beam with longer acquisition time, but increased image quality due to reduced scatter. One or more optimization processes are also applicable to all of the above embodiments to determine beam positioning, determine readout range, estimate scatter, etc.

Figure 11:
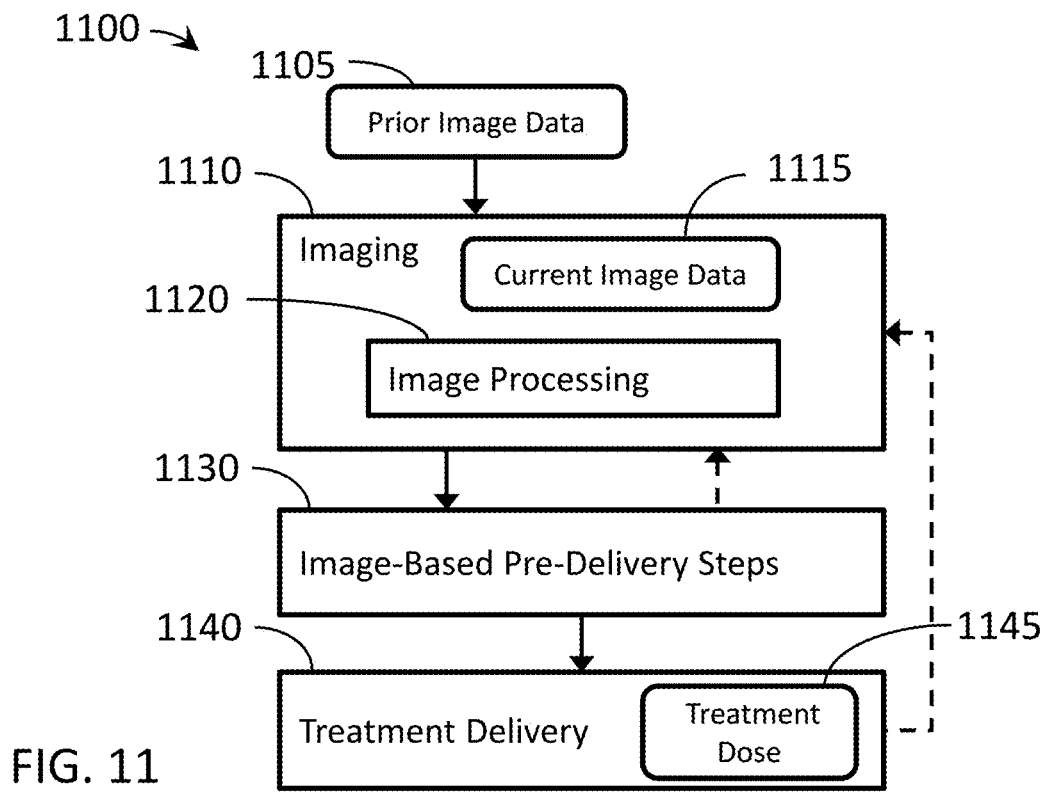
FIG. 11 is a flow chart depicting an exemplary method of IGRT using a radiotherapy device.

FIG. 11 is a flow chart depicting an exemplary method 1100 of IGRT using a radiotherapy device (including, e.g., imaging apparatus 10). Prior image data 1105 of the patient is available for use (e.g., a prior image, which may be a previously-acquired planning image, including a prior CT image, as discussed above). In some embodiments, the prior image data 1105 is generated by the same radiotherapy device, but at an earlier time. At step 1110, imaging of a patient is performed using a source of low-energy radiation (e.g., kV radiation from x-ray source 30). In one embodiment, imaging comprises a circular scan with a fan or cone beam geometry. Step 1110 can produce high-quality (HQ) image(s) or imaging data 1115 using the scatter estimation and correction techniques described above. In some embodiments, image quality may be adjusted to optimize a balance between image quality/resolution and dosage. In other words, not all images need to be of the highest quality or image quality may be adjusted to optimize or trade off a balance between image quality/resolution and image acquisition time. Imaging step 1110 can also include image processing 1120 to generate patient images based on the imaging/scan data (e.g., in accordance with methods described above). Although image processing step 1120 is shown as part of imaging step 1110, in some embodiments image processing step 1120 is a separate step, including where image processing is executed by separate devices.

Next, at step 1130, one or more image-based pre-delivery steps, discussed below, are performed based at least in part on the imaging data 1115 from step 1110. As discussed in more detail below, step 1130 can include determining various parameters associated with the therapeutic treatment and (subsequent) imaging planning. In some embodiments, image-based pre-delivery steps (1130) may require more imaging (1110) before treatment delivery (1140). Step 1130 can include adapting a treatment plan based on the imaging data 1115 as part of an adaptive radiotherapy routine. In some embodiments, image-based pre-delivery steps 1130 may include real-time treatment planning. Embodiments may also include simultaneous, overlapping, and/or alternating activation of the imaging and therapeutic radiation sources. Real-time treatment planning may involve any or all of these types of imaging and therapeutic radiation activation techniques (simultaneous, overlapping, and/or alternating).

Next, at step 1140, therapeutic treatment delivery is performed using a source of high-energy radiation (e.g., MV radiation from therapeutic radiation source 20). Step 1140 delivers a treatment dose 1145 to the patient according to the treatment plan. In some embodiments, the IGRT method 1100 may include returning to step 1110 for additional imaging at various intervals, followed by image-based pre-delivery steps (1130) and/or treatment delivery (1140) as required. In this manner the high-quality imaging data 1115 may be produced and utilized during IGRT using one apparatus 10 that is capable of adaptive therapy. As mentioned above, steps 1110, 1130, and/or 1140 may be executed simultaneously, overlapping, and/or alternating.

IGRT can include at least two general goals: (i) to deliver a highly conformal dose distribution to the target volume; and (ii) to deliver treatment beams with high accuracy throughout every treatment fraction. A third goal can be to accomplish the two general goals in as little time per fraction as possible. Delivering treatment beams accurately requires the ability to identify and/or track the location of the target volume intrafraction with high-quality images. The ability to increase delivery speed requires the ability to accurately, precisely, and quickly move the radiation source according to the treatment plan.

Figure 12:
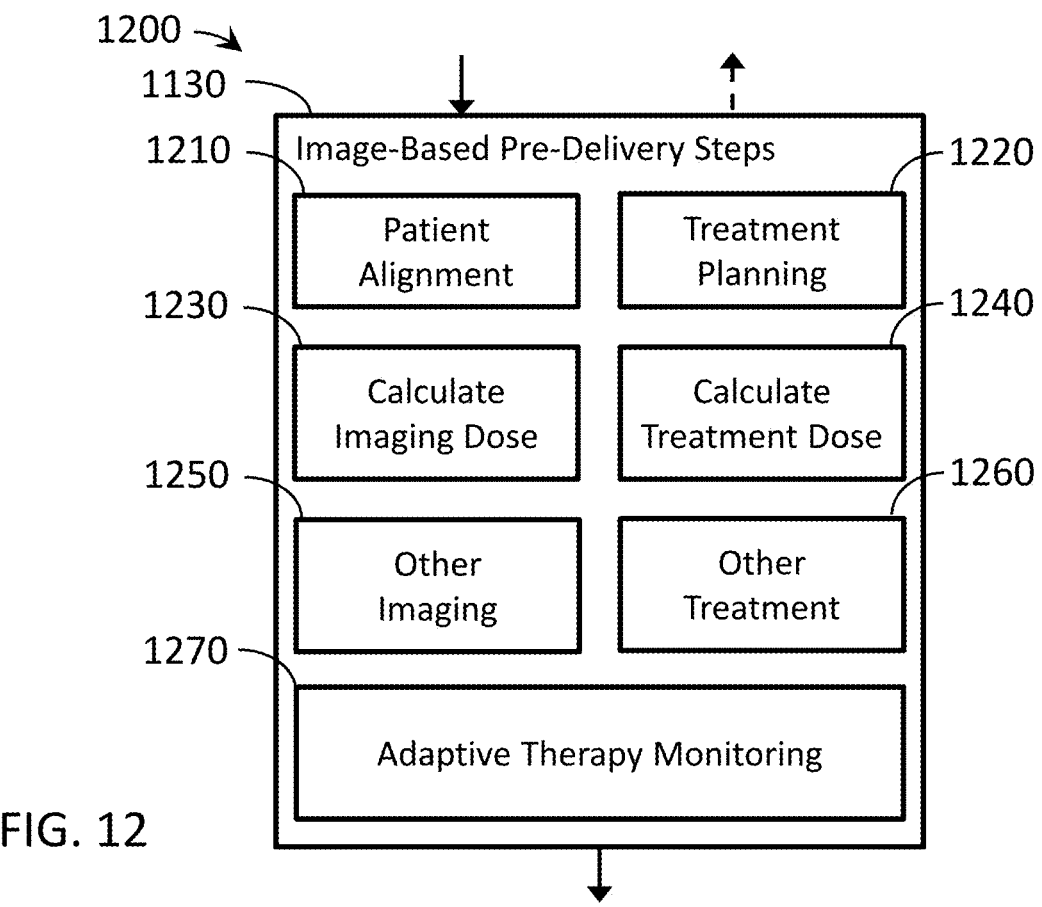
FIG. 12 is a block diagram depicting exemplary image-based pre-delivery steps.

FIG. 12 is a block diagram 1200 depicting exemplary image-based pre-delivery steps/options that may be associated with step 1130 above. It will be appreciated that the above-described imaging apparatus 10 (e.g., as part of a radiotherapy device) can generate kV images that can be used in a variety of ways, including for image-based pre-delivery steps (1130), without departing from the scope of the present invention. For example, images 1115 generated by the radiotherapy device can be used to align a patient prior to treatment (1210). Patient alignment can include correlating or registering the current imaging data 1115 with imaging data associated with earlier pre-treatment scans and/or plans, including the treatment plan. Patient alignment can also include feedback on the physical position of the patient relative to the radiation source to verify whether the patient is physically within the range of the delivery system. If necessary, the patient can be adjusted accordingly. In some embodiments, patient alignment imaging may purposely be of lesser quality to minimize dosage but provide adequate alignment information.

Images generated by the imaging apparatus 10 can also be used for treatment planning or re-planning (1220). In various embodiments, step 1220 can include confirming the treatment plan, modifying the treatment plan, generating a new treatment plan, and/or choosing a treatment plan from a set of treatment plans (sometimes referred to as "plan of the day"). For example, if the imaging data 1115 shows that the target volume or ROI is the same as when the treatment plan was developed, then the treatment plan can be confirmed. However, if the target volume or ROI is not the same, re-planning of the therapeutic treatment may be necessary. In the case of re-planning, because of the high quality of the imaging data 1115 (generated by the x-ray imaging apparatus 10 at step 1110), the imaging data 1115 may be used for treatment planning or re-planning (e.g., generating a new or modified treatment plan). In this manner, pre-treatment CT imaging via a different device is not necessary. In some embodiments, confirming and/or re-planning may be an ongoing procedure before and/or after various treatments.

In accordance with another exemplary use case, images generated by the imaging apparatus 10 can be used to calculate imaging dose (1230), which may be used for ongoing determinations of total dose to the patient and/or for subsequent imaging planning. The quality of subsequent imaging may also be determined as part of the treatment planning, for example, to balance quality and dosage. In accordance with another exemplary use case, images generated by the imaging apparatus 10 can be used to calculate treatment dose (1240), which may be used for ongoing determinations of total dose to the patient and/or may be included as part of treatment planning or re-planning.

In accordance with other exemplary use cases, images generated by the imaging apparatus 10 can be used in connection with planning or adjusting other imaging (1250) and/or other treatment (1260) parameters or plans, including, for example, as part of adaptive therapy and/or treatment plan generation. In accordance with another exemplary use case, images generated by the imaging apparatus 10 can be used in connection with adaptive therapy monitoring (1270), which can include monitoring treatment delivery and adapting as required.

It should be appreciated that the image-based pre-delivery steps (1130) are not mutually exclusive. For example, in various embodiments, calculate treatment dose (1240) can be a step by itself and/or can be part of adaptive therapy monitoring (1270) and/or treatment planning (1220). In various embodiments, the image-based pre-delivery steps (1130) can be performed automatically and/or manually with human involvement.

The devices and methods described above, including the adjustable collimation (aperture) of the image radiation and the scatter estimation and correction schemes, provide improved scatter estimation, which results in kV-generated images of higher quality than conventional in-treatment imaging systems using CBCT.

Figure 13:
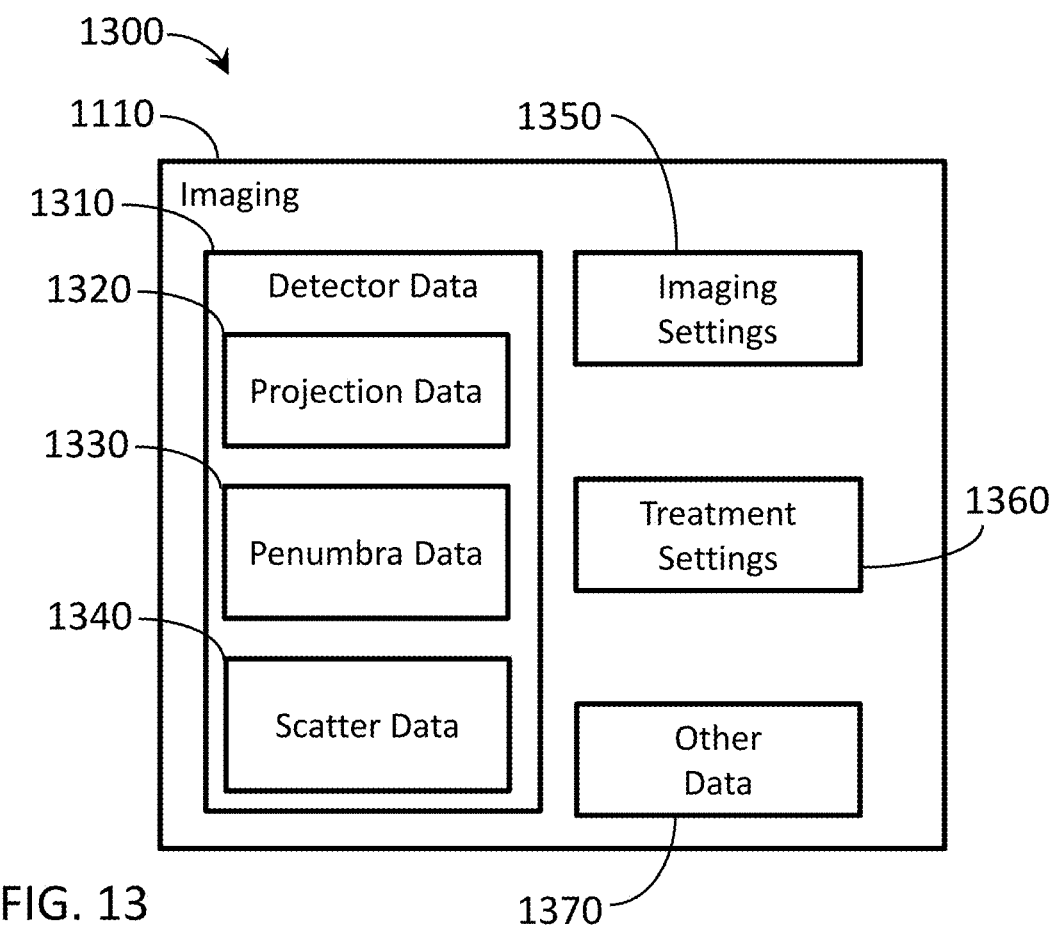
FIG. 13 is a block diagram depicting exemplary data sources that may be utilized during imaging or image-based pre-delivery steps.

FIG. 13 is a block diagram 1300 depicting exemplary data sources that may be utilized during imaging (1110) and/or subsequent image-based pre-delivery steps (1130). Detector data 1310 represents all of the data received by the image radiation detector 34. The projection data 1320 is the data generated by the radiation incident in the collimated beam area, referred to above as the scan region. The penumbra data 1330 is the data generated by the radiation incident in the penumbra area. The scatter data 1340 is the data generated by the radiation incident in the peripheral area outside of the penumbra area and/or the determined scatter as described above. In another embodiment, the scatter data 1340 can be used to determine the residual effect of the scatter from the therapeutic radiation source 20 (e.g., MV) when the two sources 20, 30 are operated simultaneously or in an interleaved manner.

In this manner, the penumbra data 1330 and/or the scatter data 1340 may be utilized to improve the quality of the images generated by the imaging step 1110. In some embodiments, the penumbra data 1330 and/or the scatter data 1340 may be combined with the projection data 1320 and/or analyzed in view of the applicable imaging settings 1350, treatment settings 1360 (e.g., if simultaneous imaging and treatment radiation), and any other data 1370 associated with the imaging apparatus 10 at the time of the data collection at the imaging detector 34. In other embodiments, the data may be used for the treatment planning step 1130.

Although the disclosed technology has been shown and described with respect to a certain aspect, embodiment or embodiments, it is obvious that equivalent alterations and modifications will occur to others skilled in the art upon the reading and understanding of this specification and the annexed drawings. In particular regard to the various functions performed by the above described elements (components, assemblies, devices, members, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary aspect, embodiment or embodiments of the disclosed technology. In addition, while a particular feature of the disclosed technology may have been described above with respect to only one or more of several illustrated aspects or embodiments, such feature may be combined with one or more other features of the other embodiments, as may be desired and advantageous for any given or particular application.

While the embodiments discussed herein have been related to the systems and methods discussed above, these embodiments are intended to be exemplary and are not intended to limit the applicability of these embodiments to only those discussions set forth herein. While the present invention has been illustrated by the description of embodiments thereof, and while the embodiments have been described in some detail, it is not the intention of the applicant to restrict or in any way limit the scope of the appended claims to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general inventive concept.

The invention claimed is:

1. An imaging apparatus, comprising:
a rotating imaging source for emitting a radiation beam;
a detector positioned to receive radiation from the imaging source; and
a beamformer configured to adjust a shape of the radiation beam emitted by the imaging source, such that the shape of the radiation beam is configured for a wide aperture scan of a wide axial region and a narrow aperture scan of a narrow axial region within the wide axial region;
a data processing system configured to at least one of:
determine an estimated scatter in the wide angle region using a first optimized scatter estimation technique based on a difference between measured scatter in the narrow axial region and estimated scatter in the narrow axial region; and
reconstruct a scatter-corrected wide region image using a second optimized scatter estimation technique based on a calculated difference between a nearly scatter-free narrow region image and a scatter-corrected narrow region image.

2. The imaging apparatus of claim 1, further comprising a data processing system configured to:
receive measured projection data in the wide axial region and the narrow axial region; and
determine the estimated scatter in the wide axial region using a kernel-based technique.

3. The imaging apparatus of claim 1, wherein the wide aperture scan and the narrow aperture scan comprise circular scans.

4. A method of estimating scatter in images, comprising:
receiving measured projection data from a wide aperture scan of a wide axial region and a narrow aperture scan of a narrow axial region within the wide axial region;
determining a measured scatter in the narrow axial region based on the narrow aperture scan projection data and the wide aperture scan projection data that overlaps the narrow axial region;
determining an estimated scatter in the narrow axial region based on the wide aperture scan projection data that overlaps the narrow axial region using a scatter estimation technique;
calculating a difference between the measured scatter in the narrow axial region and the estimated scatter in the narrow axial region;
optimizing the scatter estimation technique based on the difference between the measured scatter in the narrow axial region and the estimated scatter in the narrow axial region; and
determining an estimated scatter in the wide axial region based on the wide aperture scan projection data using the optimized scatter estimation technique.

5. The method of claim 4, wherein determining the measured scatter in the narrow axial region comprises subtracting the narrow aperture scan projection data from the wide aperture scan projection data that overlaps the narrow axial region.

6. The method of claim 4, further comprising isolating the wide aperture scan projection data that overlaps the narrow axial region from the wide aperture scan projection data.

7. The method of claim 4, further comprising isolating the estimated scatter in the narrow axial region from an estimated scatter in the wide axial region.

8. The method of claim 4, further comprising determining if the scatter estimation technique should be refined based on the difference between the measured scatter in the narrow axial region and the estimated scatter in the narrow axial region, wherein optimizing the scatter estimation technique comprises an iterative refinement process.

9. The method of claim 8, wherein determining if the scatter estimation technique should be refined comprises comparing the difference between the measured scatter in the narrow axial region and the estimated scatter in the narrow axial region to a threshold value.

10. The method of claim 4, wherein the scatter estimation technique comprises a kernel-based scatter estimation technique, and wherein optimizing the scatter estimation technique comprises constraining the kernel-based scatter estimation technique.

11. The method of claim 4, further comprising determining a location of the narrow axial region based on a prior image.

12. The method of claim 4, further comprising determining a location of the narrow axial region based on the projection data from the wide aperture scan.

13. The method of claim 4, wherein the narrow axial region comprises a plurality of narrow axial regions within the wide axial region.

14. A method of correcting scatter in images, comprising:
receiving measured projection data from a wide aperture scan of a wide axial region and a narrow aperture scan of a narrow axial region within the wide axial region;
reconstructing a scatter-free narrow region image based on the narrow aperture scan projection data;
reconstructing a scatter-corrected narrow region image based on the wide aperture scan projection data that overlaps the narrow axial region using a scatter correction technique;
calculating a difference between the scatter-free narrow region image and the scatter-corrected narrow region image;
optimizing the scatter correction technique based on the difference between the scatter-free narrow region image and the scatter-corrected narrow region image; and
reconstructing a scatter-corrected wide region image based on the wide aperture scan projection data using the optimized scatter correction technique.

15. The method of claim 14, further comprising determining if the scatter correction technique should be refined based on the difference between the scatter-free narrow region image and the scatter-corrected narrow region image, wherein optimizing the scatter correction technique comprises an iterative refinement process.

16. The method of claim 15, wherein determining if the scatter correction technique should be refined comprises comparing the difference between the scatter-free narrow region image and the scatter-corrected narrow region image to a threshold value.

17. The method of claim 14, wherein the scatter correction technique comprises a kernel-based scatter correction technique, and wherein optimizing the scatter correction technique comprises constraining the kernel-based scatter correction technique.

18. The method of claim 14, further comprising determining a location of the narrow axial region based on a prior image.

19. The method of claim 14, further comprising determining a location of the narrow axial region based on a reconstruction of the projection data from the wide aperture scan.

20. A radiotherapy delivery device comprising:
 a rotatable gantry system positioned at least partially around a patient support;
 a first source of radiation coupled to the rotatable gantry system, the first source of radiation being configured as a source of therapeutic radiation;
 a second source of radiation coupled to the rotatable gantry system, the second source of radiation being configured as a source of imaging radiation having an energy level less than the source of therapeutic radiation;
 a radiation detector coupled to the rotatable gantry system and positioned to receive radiation from the second source of radiation;
 a beamformer configured to adjust a shape of a radiation beam emitted by the second source of radiation, such that the shape of the radiation beam is configured for a wide aperture scan of a wide axial region and a narrow aperture scan of a narrow axial region within the wide axial region; and
 a data processing system configured to:
  receive measured projection data in the wide axial region and the narrow axial region;
  and
  at least one of:
   reconstruct a patient image using an estimated scatter, the estimated scatter determined via a first kernel-based optimized scatter estimation technique based on a difference between measured scatter in the narrow axial region and estimated scatter in the narrow axial region; and
   reconstruct a patient image using a second kernel-based optimized scatter estimation technique based on a calculated difference between a nearly scatter-free narrow region image and a scatter-corrected narrow region image; and
  deliver a dose of therapeutic radiation to the patient via the first radiation source based on the patient image during adaptive IGRT.

* * * * *